United States Patent
Lerner et al.

(10) Patent No.: US 12,133,811 B2
(45) Date of Patent: Nov. 5, 2024

(54) DIFFERENTIAL AND VARIABLE STIFFNESS ORTHOSIS DESIGN WITH ADJUSTMENT METHODS, MONITORING AND INTELLIGENCE

(71) Applicant: Arizona Board of Regents on Behalf of Northern Arizona University, Flagstaff, AZ (US)

(72) Inventors: Zachary F Lerner, Flagstaff, AZ (US); Grigoriy Orekhov, Flagstaff, AZ (US); Leah Liebelt, Flagstaff, AZ (US)

(73) Assignee: ARIZONA BOARD OF REGENTS ON BEHALF OF NORTHERN ARIZONA UNIVERSITY, Flagstaff, AZ (US)

( * ) Notice: Subject to any disclaimer, the term of this patent is extended or adjusted under 35 U.S.C. 154(b) by 161 days.

(21) Appl. No.: 17/515,300

(22) Filed: Oct. 29, 2021

(65) Prior Publication Data
US 2022/0133519 A1 May 5, 2022

Related U.S. Application Data

(60) Provisional application No. 63/215,336, filed on Jun. 25, 2021, provisional application No. 63/107,275, filed on Oct. 29, 2020.

(51) Int. Cl.
*A61F 5/01* (2006.01)

(52) U.S. Cl.
CPC .... *A61F 5/0127* (2013.01); *A61F 2005/0155* (2013.01); *A61F 2005/0167* (2013.01); *A61F 2005/0179* (2013.01)

(58) Field of Classification Search
CPC ...... A61F 2002/5018; A61F 2002/5072; A61F 5/0102; A61F 5/0113; A61F 2005/0155; A61F 2005/0167; A61F 2005/0169; A61F 5/0585; A61F 5/01–0116; A61F 5/0123–0127; A61F 5/0193; A61F 2005/0132–0179; A61F 2005/0197; A61F 2/50; A61F 2/60; A61F 2/604–6607;
(Continued)

(56) References Cited

U.S. PATENT DOCUMENTS

| | | | |
|---|---|---|---|
| 5,058,574 A * | 10/1991 | Anderson | A61F 5/0125 602/26 |
| 7,578,799 B2 | 8/2009 | Thorsteinsson et al. | |
| 8,075,633 B2 | 12/2011 | Herr et al. | |

(Continued)

FOREIGN PATENT DOCUMENTS

CN  106826763  6/2017

*Primary Examiner* — Tarla R Patel
(74) *Attorney, Agent, or Firm* — Quarles & Brady LLP

(57) ABSTRACT

An assistive ankle foot orthosis is described. The AFO has a tubular vertical member arranged laterally to a user's limb. The member carries a rotational bearing and a rotational element such as a pulley. The pulley is connected to a footplate. The footplate provides joint movement assistance or resistance to the user upon rotation of the pulley. The pulley is coupled to one or more springs that provide counter-rotational resistance to pulley movement, thereby storing, and then returning, rotational force during certain foot movements. The spring can include a leaf spring arranged inside the member, the stiffness of which can be manually, automatically or dynamically adjusted by movement of the device.

16 Claims, 15 Drawing Sheets

(58) Field of Classification Search
CPC . A61H 3/00; A61H 1/02; A61H 1/0237–0266
See application file for complete search history.

(56) References Cited

U.S. PATENT DOCUMENTS

| | | | |
|---|---|---|---|
| 8,114,034 B2 | 2/2012 | Ikeuchi et al. | |
| 8,267,876 B2* | 9/2012 | Ashihara | A61H 3/008 601/34 |
| 8,419,804 B2 | 4/2013 | Herr et al. | |
| 9,597,217 B2 | 3/2017 | Patton et al. | |
| 9,788,985 B2 | 10/2017 | Dollar et al. | |
| 10,076,462 B2 | 9/2018 | Johnson et al. | |
| 10,179,079 B2 | 1/2019 | Strausser et al. | |
| 10,517,788 B2 | 12/2019 | Lee et al. | |
| 10,561,564 B2 | 2/2020 | LaChappelle et al. | |
| 10,729,610 B2 | 8/2020 | Matthew et al. | |
| 2003/0115031 A1 | 6/2003 | Dariush et al. | |
| 2004/0249316 A1 | 12/2004 | Ashihara et al. | |
| 2005/0059908 A1 | 3/2005 | Bogert | |
| 2005/0097970 A1 | 5/2005 | Nurse | |
| 2007/0027421 A1* | 2/2007 | Nobbe | A61F 5/0113 128/882 |
| 2008/0319361 A1 | 12/2008 | Messer | |
| 2010/0063424 A1 | 3/2010 | Kudoh et al. | |
| 2010/0164728 A1 | 7/2010 | Plost | |
| 2011/0028871 A1 | 2/2011 | Shishido | |
| 2011/0213599 A1 | 9/2011 | Jacobsen et al. | |
| 2011/0214524 A1 | 9/2011 | Jacobsen et al. | |
| 2011/0264238 A1 | 10/2011 | van der Merwe et al. | |
| 2011/0295164 A1 | 12/2011 | Jacobsen et al. | |
| 2012/0289870 A1 | 11/2012 | Hsiao-Wecksler et al. | |
| 2012/0293323 A1 | 11/2012 | Kaib et al. | |
| 2012/0330395 A1 | 12/2012 | Dar et al. | |
| 2013/0006159 A1 | 1/2013 | Nakashima et al. | |
| 2013/0053736 A1 | 2/2013 | Konishi | |
| 2013/0158444 A1 | 6/2013 | Herr et al. | |
| 2013/0226048 A1 | 8/2013 | Unluhisarcikli et al. | |
| 2013/0289452 A1 | 10/2013 | Smith et al. | |
| 2014/0100492 A1 | 4/2014 | Nagasaka | |
| 2014/0200491 A1 | 7/2014 | Julin et al. | |
| 2014/0260950 A1 | 9/2014 | Cook | |
| 2015/0321342 A1 | 11/2015 | Smith et al. | |
| 2015/0374573 A1 | 12/2015 | Horst et al. | |
| 2016/0045385 A1 | 2/2016 | Aguirre-Olliger et al. | |
| 2016/0143800 A1 | 5/2016 | Hyung et al. | |
| 2016/0296345 A1 | 10/2016 | Deshpande et al. | |
| 2017/0119613 A1 | 5/2017 | Roh et al. | |
| 2017/0196751 A1 | 7/2017 | Smith et al. | |
| 2017/0202725 A1 | 7/2017 | Robertson et al. | |
| 2017/0273853 A1 | 9/2017 | Nagata et al. | |
| 2018/0055711 A1 | 3/2018 | Choi et al. | |
| 2018/0085277 A1 | 3/2018 | Julin | |
| 2018/0085280 A1 | 3/2018 | Shimada et al. | |
| 2018/0092536 A1 | 4/2018 | Sandler et al. | |
| 2018/0116851 A1 | 5/2018 | Lee | |
| 2018/0161188 A1 | 6/2018 | Zistatsis et al. | |
| 2018/0168907 A1 | 6/2018 | Huang et al. | |
| 2018/0177672 A1 | 6/2018 | Uchida et al. | |
| 2019/0015286 A1* | 1/2019 | Glaister | A61F 2/604 |
| 2019/0105215 A1 | 4/2019 | Dalley et al. | |
| 2019/0105777 A1 | 4/2019 | Dalley et al. | |
| 2019/0192373 A1 | 6/2019 | Vouga et al. | |
| 2019/0232485 A1 | 8/2019 | Reese | |
| 2019/0343710 A1 | 11/2019 | Lemer | |
| 2019/0344433 A1 | 11/2019 | Lerner | |
| 2020/0039061 A1 | 2/2020 | Sankai | |
| 2021/0369536 A1 | 12/2021 | Mooney et al. | |
| 2021/0378904 A1 | 12/2021 | Lerner et al. | |
| 2022/0000703 A1 | 1/2022 | Lerner et al. | |
| 2022/0079833 A1 | 3/2022 | Lerner | |

\* cited by examiner

DIFFERENTIAL AND VARIABLE STIFFNESS ORTHOSIS DESIGN WITH ADJUSTMENT METHODS, MONITORING AND INTELLIGENCE

CROSS-REFERENCE TO RELATED APPLICATIONS

This application claims priority to U.S. Provisional Application 63/107,275 entitled "Differential and Variable Stiffness Orthosis Design With Adjustment Methods, Monitoring and Intelligence", filed on Oct. 29, 2020, the disclosure of which is incorporated in its entirety herein by reference. This application also claims priority to U.S. Provisional Application 63/215,336 entitled "Parallel Elastic Leaf Spring for Cable-Actuated Lower Extremity Exoskeleton", filed on Jun. 25, 2021, the disclosure of which is incorporated in its entirety herein by reference.

STATEMENT CONCERNING FEDERALLY-FUNDED RESEARCH

This invention was made with government support under Grant No. 1R15HD099664 awarded by the National Institutes of Health. The government may have certain rights in the invention.

BACKGROUND

A number of injuries or conditions can lead to disorders that affect muscle control. Individuals with muscle control disorders frequently experience a downward trend of reduced physical activity and worsening of gait function leading to a permanent decline in ambulatory ability. Upper- or lower-extremity orthoses, including ankle foot orthoses (AFOs), are commonly prescribed for individuals who suffer from such muscle control disorders, or other impairments, as from stroke, incomplete spinal cord injury and cerebral palsy. These devices provide mobility enhancement by applying assistive joint torque through the gait cycle. Existing devices use a variety of design approaches to accomplish this fundamental aim. These devices may include Bowden cable actuation, direct-drive shank mounted motors, fabric shank interfaces, bilateral carbon fiber frames, and lateral lower leg structures. Certain devices can also be used for training or strengthening aids, by providing active resistance during some or all phases of the gait cycle.

AFOs generally include footplates to direct torsional force provided at the angle toward the ground, or additionally alternatively, to resist torsional forces imparted by the user's ankle joint. The footplate is located beneath the user's foot, and between the user's foot and the ground, typically on the foot bed of a shoe worn by the user. In addition to constituting a force transmitting interface between the user's foot and the ground, in the case of active devices, the foot plate typically carries one or more sensors, such as pressure sensors, which may measure the force being applied to the foot plate or the ground by the user of the device. Inventive embodiments below describe certain improvements to passive, quasi-passive and active AFOs.

BRIEF SUMMARY

Embodiments of the invention are directed to a passive or active ankle foot orthosis for assisting with ankle motion, training, rehabilitation and the like. The AFO includes an adjustable tensioning component (e.g., one or more springs) coupled to a transmission linkage (e.g., a set of Bowden cables, chain, etc., or a tab), and an extended vertical member coupled to a user's leg via, e.g., a calf cuff. A rotatable bearing is mounted within the member, and is rotatable by a pulley connected to the cables. The bearing is coupled to a footplate, and is rotatable in a plantar direction or a dorsal direction by a wearer. Motion in these directions can be assisted or resisted depending on the tension applied to the cables by the tensioning component. In particular, a tensioning component like a spring can store energy during a portion of the ankle rotation, and then the energy as assistive torque when the rotation is reversed. In certain embodiments, the extended vertical member is a tubular member having a closed, circumferential cross section, and the bearing is located within the interior space defined by the walls or wall of the tubular member. In preferred embodiments, the vertical member is arranged laterally with respect to the user's leg, and the rotational bearing is arranged such that its axis of rotation is coincident with the user's ankle. In preferred embodiments described below, tensioning components allow for active or passive tensioning, and they provide an assistive or resistive torque bias to the footplate coupled to the rotational bearing.

In one aspect, the invention includes a novel joint orthosis design having differential and or variable stiffness via manual, automated, or passive mechanical adjustment.

In one aspect, the invention is directed to a joint orthosis such as an AFO. The AFO includes a modular, laterally-mounted hinged design, which is to say, that the point of rotation of the orthosis is lateral to the user's ankle. The orthosis is comprised of a distal attachment component, an "upright" component that mounts laterally to the joint (for AFO designs), a hinge mechanism located in line with the joint, and a proximal attachment point. The distal attachment component may include a footplate, and the proximal attachment point may include a calf-cuff. The distal and proximal attachment components may be swapped out for difference sizes. The upright may be comprised of a rigid carbon fiber circular, oval, rectangular, hexagonal, square or other polygonal tube. The hinge mechanism may incorporate a pulley or cam placed within the upright tube that rotates relative to tube through bearings or bushings. The lateral upright design allows for modularity of the components, minimizes medially-protruding features that cause contact with other parts of the body, and minimizes anterior or posterior protruding features that may cause contact with objects in the environment.

In another aspect, the AFO includes differential stiffness spring components, for example, linear, compression, rotary, or leaf springs, for the flexion (dorsi extension) and extension (plantar extension) directions. In an assistive configuration, a spring component may be engaged such that the orthosis resists extension during the stance phase and/or resists flexion during the swing phase. In a training configuration, these forces may be reversed. For lower-extremity (e.g., AFO) configurations there may be stance phase spring engagement and/or swing phase spring engagement.

In certain embodiments, AFO's according to the invention exhibit velocity-dependent stiffness. In such embodiments, the orthosis may include a damping mechanism in the flexor or extensor directions to provide automatic velocity-dependent stiffness adjustments. Such embodiments may provide added stiffness when the user is running, for example. Alternative spring configurations are provided for flexion or extension resistance. For lower-extremity embodiments, the orthosis spring components may be configured to provide extension resistance during the stance phase and/or flexion resistance during the swing phase.

AFO's having tensioning springs according to described embodiments have adjustable flexion and extension equilibrium angles, which are the angles at which the flexion or extension spring component becomes engaged. The springs can be configured so that the equilibrium angle is the same or different for the flexion and extension directions.

Similarly, some embodiments allow for quick, manual adjustment to the flexion and extension spring stiffnesses through turning a knob, adjusting a slider, lever, or other similar mechanism, without the need of hand or power tools. In additional embodiments, components or mechanisms are included to adjust the flexion or extension spring stiffnesses based on joint angle, walking terrain, locomotor condition (walking, running) or speed. Spring stiffness could be adjusted by adding or subtracting linear springs in parallel, pre-loading a rotational spring, or adjusting the pivot point on a leaf spring. In some orthoses of the of the aforementioned mechanical designs, components may or may not include a small actuator (e.g., DC motor) to adjust the spring stiffness, equilibrium angle, or assist/resist mode of operation.

In some configurations, mounted within or outside of the upright, the spring components may include linear extension springs, linear compression springs, leaf springs (e.g., an elastic carbon fiber bar), linear, non-linear, or constant force rotary springs.

In certain embodiments, variable stiffness AFO's include a variety of sensors and data processing components usable to determine how to adjust stiffness. In such embodiments, the orthosis includes the necessary electromechanical and software features (e.g., microprocessor, sensors and wireless connectivity, cloud server), making it a connected, intelligent orthosis. By tracking sensor data about the user's ankle position, velocity and acceleration, foot pressure, and the linear and angular acceleration of the AFO itself, such embodiments can provide intelligent recommendations for adjustment of stiffnesses or equilibrium angles. The recommendations may be provided to a user, who may manually adjust the device, or to the user's clinical or rehab team, or the device may automatically adjust the device to improve device function and performance.

In one embodiment, a wearable assistive device is described. The device has an extended, tubular structural member having a closed circumferential cross section, a first end and a second end defining a long axis through a center of the extended structural member. The device includes an attachment device coupled to the member and extending medially from the member, the attachment device configured to secure the member to a limb of a user. The device also has a rotational bearing disposed within the extended structural member and positioned on the long axis near the second end of the extended structural member. The device includes a pulley coupled to the rotational bearing, and a footplate dimensioned to support a foot of a wearer of the assistive device and coupled to the pulley such that it may rotate with respect to the long axis of the extended tubular member. The device also has a first cable having a first end and a second end, the first end coupled to a first spring, the second end coupled to the pulley.

Another embodiment is directed to an alternative wearable assistive device. The device has an extended, hollow, tubular structural member having a closed circumferential cross section, a first end and a second end defining a long axis through a center of the extended structural member. The device also has an attachment device coupled to the member and extending medially from the member, the attachment device configured to secure the member to a limb of a user. There is a rotational bearing disposed within the extended structural member and positioned on the long axis near the second end of the extended structural member, and a rotational element coupled to the rotational bearing. The device includes a footplate dimensioned to support a foot of a wearer of the assistive device and coupled to the rotational element such that it may rotate with respect to the long axis of the extended tubular member. The device also includes a leaf spring arranged within the hollow, tubular member, and a cable having a first end and a second end, the first end coupled to the leaf spring and the second end coupled to the rotational element.

AFOs according to inventive embodiments have certain advantages, which are also applicable to assistive orthoses for other joints. For example, the embodiments described below improve the ability of an individual to fit a device and perform self-calibration or customization of the amount and angle of joint support (i.e., stiffness) without the need to visit a certified orthoptist. The self-adjustability of the device permits a user to dial-in different support quantities or change the angle as the user progresses throughout a rehabilitation program, or encounters different sorts of walking terrain (i.e., flat areas versus hilly areas). Additionally, inventive embodiments accommodate interchangeable components (e.g., springs, vertical members or footplates) that can be swapped out for larger/smaller sizes. Inventive embodiments provide the option for user and device monitoring and are usable to create a connected device that can be used for telerehab or telemedicine. Additionally, the device modifications described herein are usable to optimize performance across different ambulatory conditions. Additional advantageous will become clear upon consideration of the detailed description of the preferred embodiments taken in conjunction with the accompanying drawings.

BRIEF DESCRIPTION OF THE DRAWINGS

The drawings described herein constitute part of this specification and includes exemplary embodiments of the present invention which may be embodied in various forms. It is to be understood that in some instances, various aspects of the invention may be shown exaggerated or enlarged to facilitate an understanding of the invention. Therefore, drawings may not be to scale.

DETAILED DESCRIPTION OF THE PREFERRED EMBODIMENTS

The described features, advantages, and characteristics may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments.

Reference throughout this specification to "one embodiment," "an embodiment," or similar language means that a particular feature, structure, or characteristic described in connection with the embodiment is included in at least one embodiment. Thus appearances of the phrase "in one embodiment," "in an embodiment," and similar language throughout this specification may, but do not necessarily, all refer to the same embodiment. References to "users" refer generally to individuals accessing a particular computing device or resource, to an external computing device accessing a particular computing device or resource, or to various processes executing in any combination of hardware, software, or firmware that access a particular computing device or resource. Similarly, references to a "server" refer generally to a computing device acting as a server, or processes executing in any combination of hardware, software, or firmware that access control access to a particular computing device or resource.

Figure 1:
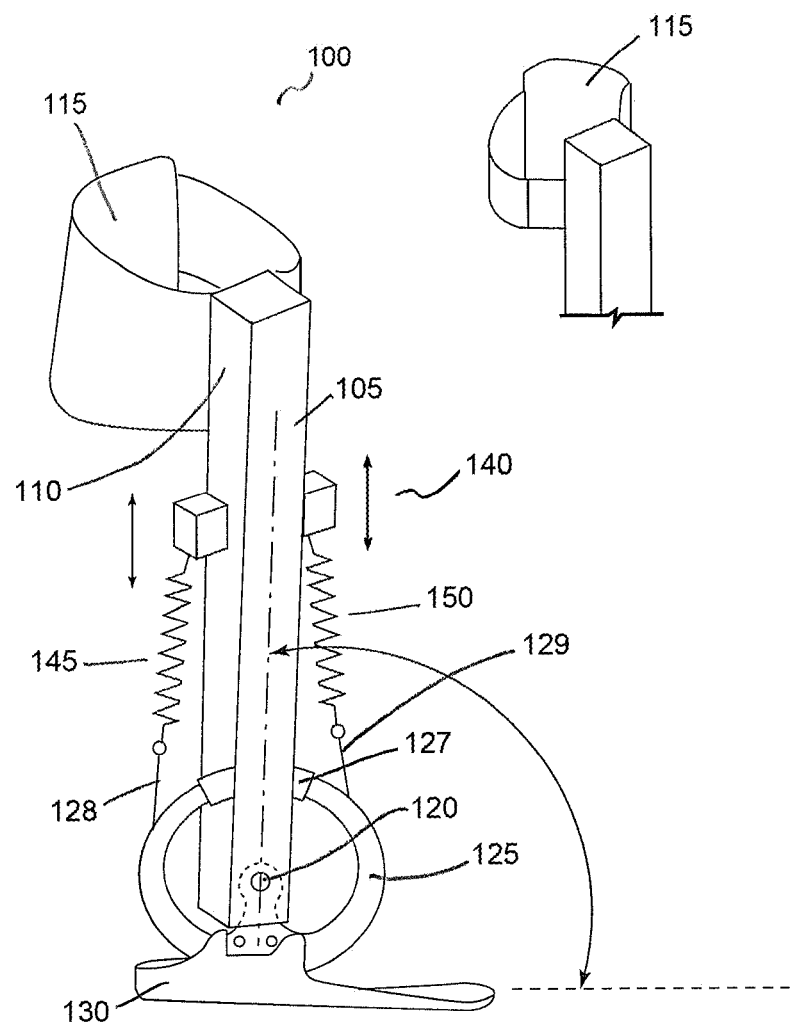
FIG. 1 depicts one embodiment of a novel ankle foot orthosis with interchangeable components, and differential and variable spring stiffness (top). Potential ankle pulley component designs (bottom).
Figure 1:

For purposes of description herein, the terms "upper," "lower," "right," "left," "rear," "front," "vertical,", "upright", "horizontal," and derivatives thereof shall relate to the embodiment of the invention as oriented in FIG. 1. However, it is to be understood that the invention may assume various alternative orientations, except where expressly specified to the contrary. It is also to be understood that the specific devices and processes illustrated in the attached drawings, and described in the following specification are simply exemplary examples of the inventive concepts defined in the appended claims. Hence, specific dimensions and other physical characteristics relating to the examples disclosed herein are not to be considered as limiting, unless the claims expressly state otherwise.

As required, detailed examples of the present invention are disclosed herein. However, it is to be understood that the disclosed examples are merely exemplary of the invention that may be embodied in various and alternative forms. The figures are not necessarily to a detailed design and some schematics may be exaggerated or minimized to show function overview. Therefore, specific structural and functional details disclosed herein are not to be interpreted as limiting, but merely as a representative basis for teaching one skilled in the art to variously employ the present invention.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

As used herein, the term "and/or," when used in a list of two or more items, means that any one of the listed items can be employed by itself, or any combination of two or more of the listed items can be employed. For example, if any assembly or composition is described as containing components A, B, and/or C, the assembly or composition can contain A alone; B alone; C alone; A and B in combination; A and C in combination; B and C in combination; or A, B, and C in combination.

As used herein, the terms "assistance" and "resistance" may be used interchangeably to signify the direction of external torque applied to a joint that may be perceived as augmenting (making a movement easier, assistance) or harder (resistance).

The following disclosure relates to an AFO comprised of a footplate component, an "upright" component that mounts laterally to the lower limb, a hinge mechanism located in line with the ankle joint, and a calf attachment point. The footplate is interchangeable and can be swapped out for different sizes. The calf attachment component could be a "calf cuff" or "shin cuff" that incorporates a rigid or semi-rigid shell with a soft (e.g., foam) lining; the calf attachment can be adjust up or down the limb and be interchanged for different sizes. The upright may be comprised of a rigid carbon fiber circular, oval, rectangular, hexagonal, square or other polygonal tube. The hinge mechanism may incorporate a pulley, cam, sprocket or a combination of these placed within the upright tube that rotates relative to upright through bearings or bushings. The lateral upright design, quick release features and component modularity of the design allows the AFO to grow with a child. In some configurations, mounted within or outside of the upright, the spring components may include linear extension springs, linear compression springs, leaf springs (e.g., elastic carbon fiber bar), linear, non-linear, or constant force rotary springs. A clutch or engaging/disengaging ratchet may be used to differentially adjust spring timing.

The AFO may include different joint stiffness components (e.g., a linear, compression, rotary, or leaf spring) for the plantar-flexion direction (pointing toes downward) and the dorsi-flexor direction (pointing toes upward), so that the plantar-flexor direction is stiffer than the dorsi-flexor direction. In an assistive configuration, a spring component may be engaged such that the AFO resists extension during the stance phase and/or resists flexion during the swing phase. In a resistive configuration, a spring component may be engaged such that the AFO resists plantar-flexion during the stance phase and/or resists dorsi-flexor during the swing phase. The AFO may have adjustable plantar-flexor and dorsi-flexor equilibrium angles.

In one embodiment of a quasi-passive novel AFO, a small DC motor actuates a mechanism to adjust the equilibrium angles and/or spring stiffnesses in the plantar- and/or dorsi-flexor directions. In another configuration, the AFO may include knobs, levers, or sliders to easily customize and adjust plantar- or dorsi-flexor spring function.

In one embodiment, the intelligent AFO tracks user and device function, automates recommendations for device settings, performs adjustments or instructs the user how to make adjustments. The device streams use and compliance information to a cloud-based server for monitoring by the clinician and insurance company.

Referring now to FIG. 1, there is shown a schematic diagram of a variable tension AFO according to an inventive embodiment. In the embodiment of FIG. 1 an AFO 100 includes a rigid upright member 105. Member 105 is preferably a hollow tubular member formed of carbon fiber or the like, having a square, rectangular, other polygonal, circular or elliptical cross section. Member 105 may have a constant or variable cross section throughout its length. Member 105 includes at a proximal end a first attachment point 110, which receives an attachment device 115 such as a calf cuff. Attachment device 115 may alternatively be a shin cuff (pictured at right), or may be an attachment device capable of securing AFO 100 to some other limb or some other portion of the leg. In a preferred embodiment, attachment device 115 is attached to member 105 by a rigid but detachable mechanism, such as fasteners that secure device 115 to member 105 through non-illustrated fastener holes. Thus, attachment device 115 is replaceable, such that the AFO may be configured for users having legs of different sizes. In one embodiment, attachment device 115 may be attached at a plurality of positions along the proximal area of member 105 to allow for adjustment of the distance between attachment device 115 and rotational bearing 120. Adjusting the position of cuff 115 with respect to rotational bearing 120 allows the user to mount AFO to the user's leg such that rotational bearing is preferably positioned such that its rotational axis is through the user's ankle. In a preferred embodiment, when worn, the member 105 of the AFO is located on the lateral side of a user's leg, and device 115 is oriented on member 105 to engage with the leg of the user to position member 105 on a medial side of the user's leg. That is to say, device 115 may extends medially from member 105.

AFO 100 also includes a rotational bearing 120, which engages with a pulley, cam, sprocket or some other rotational hinge element 125 such that rotational hinge element 125 is secured to and may rotate with respect to member 105. Preferably, the member 105 has a long axis that passes through and is perpendicular to an axis of rotation of bearing 120. In one embodiment rotational element 125 is a circular pulley that is mounted to rotational bearing 120 such that its lateral and medial sides are both located within the perimeter walls of the member 105. In such cases, member 105 may include one or more apertures (130) allowing passage of a portion of the pulley sheave through the member 105. Additionally, pulley 125 may include a component 127 of its sheave to selectively render the perimeter of the sheave discontinuous so as to facilitate installation of the pulley 125 into member 105 before it is secured to bearing 120. Component 127 may be, for example, a removable portion of the sheave, or a translating or swinging gate that opens a gap in the sheave. In the illustrated arrangement, the rotational bearing, and therefore the pulley, is supported on both ends by walls of the tubular member 105, which preferably is made of a stiff material like carbon fiber. This gives the pulley bilateral support, which is useful to prevent out of plane deflection of the pulley when the pulley is being actuated by cables, from either the passive spring components, or when used with active drive cables. Co-pending, co-owned U.S. patent application Ser. No. 17/343,628 entitled "CABLE-ACTUATED, KINETICALLY-BALANCED, PARALLEL TORQUE TRANSFER EXOSKELETON JOINT ACTUATOR WITH OR WITHOUT STRAIN SENSING" describes acceptable, exemplary configurations of AFOs having vertical members and pulleys which are usable in conjunction with embodiments described herein. That reference is incorporated herein in its entirety.

The AFO 100 of FIG. 1 also includes a footplate or insole bracket 130 attached to rotational element 125. The footplate 130 extends medially, and is configured and arranged to engage with the bottom of a user's foot when the AFO is worn. Footplate 130 may provide rotational force (i.e., torque) to a user's foot, tending to assist or resist ankle flexion or extension, when torque is applied to pulley 125. Footplate 130 is detachable from pulley 125, e.g., by one or more fasteners, such that it may be replaced in the event of wear or the desire to change the footplate's size or shape. Acceptable footplate configurations usable with the embodiments described herein are described in co-pending, co-owned U.S. patent application Ser. No. 17/365,768 entitled "OPTIMIZED ANKLE EXOSKELETON FOOT PLATE FUNCTION AND GEOMETRY", the entirety of which is incorporated herein by reference.

AFO 100 includes a bias and tensioning mechanism, 140, which provides assistive or resistive torque to pulley 125 within certain ranges of rotation of footplate 130. In the embodiment of FIG. 1, one or more linear springs (145, 150) are provided that engage a first side and a second side of the sheave of pulley 125 via cables (128, 129), cord, ribbon, chain or some other tensile force transmission mechanism. As can be seen, spring 145, depending on its vertical position and configuration, will tend to provide extending torque to footplate 130 (i.e., to cause plantar extension or resist flexion/dorsi extension), and spring 150, will tend to provide flexion torque to footplate 130 (i.e., to cause dorsi extension and resist plantar extension). Thus, in an assistive configuration, the AFO of FIG. 1 includes at least one spring component that may be engaged such that the orthosis resists extension during the stance phase and/or resists flexion during the swing phase. Providing a pair of springs enables a stance phase spring engagement and a swing phase spring engagement.

Springs 145, 150 are mounted to member 105 at one of a plurality of attachment points along the front or back (i.e., anterior or posterior) surfaces of the member 105. The provision of a plurality of vertically spaced apart attachment points permit the springs to be biased such that the torsional force provided to the pulley 125 may be varied, both in terms of magnitude, and in terms of setting the pulley's equilibrium position for each spring. Some exemplary arrangements along these lines will now be described.

One function of the arrangement of springs 145, 150 is to set the equilibrium position of footplate 130. The equilibrium position of footplate 130 is the position (i.e., the rotational state) of the footplate when it is not being acted on by external spring forces (other than the forces inherent in non-spring portions of the AFO itself, that is, the friction of the rotational bearing, and gravity acting on the footplate, etc.). The footplate will be in its equilibrium positon when the AFO device is, for example, suspended, as in when it is held by the upright member. In one embodiment, when the footplate is in its equilibrium position, the spring forces acting on the pulley are equal and balanced, and the ankle of a user wearing the AFO will receive no extension or flexion assistive or resistive force when the footplate is in the equilibrium position. The positions (along the upright member), and the spring strength (e.g., the spring constant of each spring) may chosen to set the equilibrium positon of the footplate at any angle achievable by the physical constraints of the AFO. For example, if both springs equal, and both are anchored to the same position along the upright member, and at equal complimentary positions along the pulley sheaf, the force that each spring exerts on the pulley will be equal. This will be the case regardless of whether or the extent to which the springs are extended, because the degree of each spring's extension will be equal. This arrangement will balance the rotational forces acting on the pulley when the footed is in a horizontal orientation, as shown in FIG. 1. Again, a user wearing the device when the footplate is in this position (i.e., the standing during the stance stage of the gait) will experience no auxiliary torque.

In another aspect, the AFO has adjustable flexion and extension equilibrium angles (i.e., a different footplate equilibrium position for each direction of rotation, set by each spring). Here, the equilibrium angles are the pulley angles or rotation positions at which the flexion or extension spring components become engaged. Referring again to FIG. 1, both springs are associated with the same 0 degree equilibrium angle, and the first spring 145 is engaged upon flexion from 0 degrees, and the second spring 150 is engaged upon extension from zero degrees.

Referring still to the operation of the FIG. 1 embodiment, as set forth above, there is no assistance provided in the stance phase. As the user transitions through mid-stance to toe-off, the shank rotates forward, the heel comes up, and the foot rocks forward over the toes. In the AFO of FIG. 1, during this movement, spring 150 will elongate and exert flexion torque on the footplate, tending to return it to equilibrium position. Such force may be useful to provide flexion assistance to a user's foot as it comes off the ground, as to return it to a level position. Such torque may also be helpful as a training aide—to force the user to push the foot down with more force to complete the movement prior to toe-off. Similarly, spring 145 may exert extension assistive force tending to return the footplate to equilibrium when the user is rotating the footplate up or dorsally. Such force may be helpful in rotating the foot to horizontal after the heel strike phase of the gait. Such force may also be useful as a training aid—to force the user to rotate the foot up with more force prior to heel-strike. By adjusting the spring weight, the user can vary the amount of resistance and assistance provided. By adjusting the spring positions, the user can change the equilibrium point, and therefore, can vary the points in the gait cycle where resistance and assistance are provided.

Additionally, as will be explained below in reference to FIG. 2, by adjusting the positions of the springs, and the equilibrium points of the springs, the user can create a non-linear stiffening or softening response to the resistance/ assistance. This is accomplished by shifting the relative equilibrium points of the springs such that they overlap, meaning that one spring will be counteracting the effect of the other spring during at least some portion of the movement.

In alternative embodiments, the orthosis may have a clutch or engaging/disengaging ratchet mechanism on either the flexion spring component or the extension spring component such that it engages or disengages at different angles.

As noted above, the rotational hinge element may take a number of acceptable forms. In some configurations, the hinge mechanism may be a circular pulley (constant radius) or cam pulley (non-constant radius) such that the radius may or may not be constant on the flexion or extension rotational directions. In one embodiment, the variation of radius with angle is different on one side of the pulley versus the other side (such that the sheave does not have symmetry about its centerline). A cam pulley allows for adjustments to joint stiffness as a function of the ankle joint angle. In some configurations, the hinge mechanism may be a toothed-sprocket that engages other sprockets. The main hinge component may be comprised of two separate sprockets, one to engage a flexion sprocket and another to engage an extension sprocket. The secondary sprockets would directly or indirectly apply a resistive or assistive spring force or torque to the main sprocket/hinge mechanism.

Figure 2:
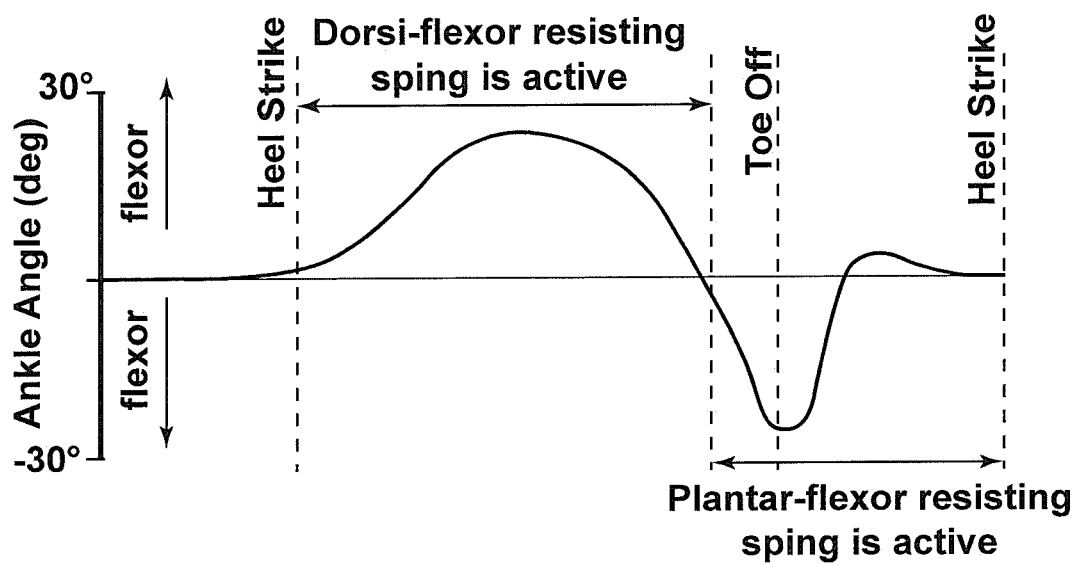
FIG. 2 depicts equilibrium angle and potential linear, stiffening, or softening spring force responses.
Figure 2:
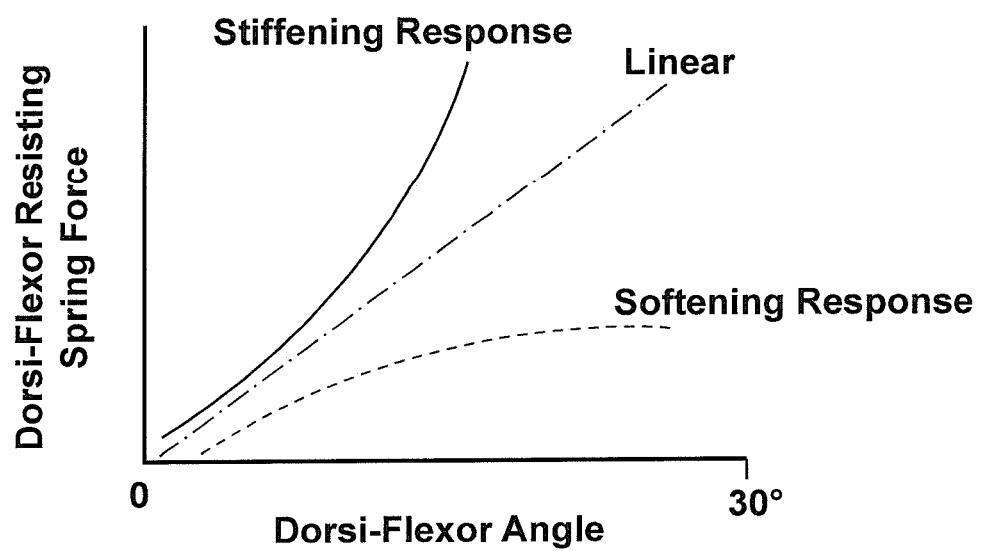

FIG. 2 shows an example of the application of torsional force by the AFO as shown in FIG. 1 having a 0 degree equilibrium position (i.e., a level footplate). As can be seen, at heel strike, the foot is rotated up, in dorsi extension (referred to above as flexion). In this position, spring 145 is in tension, making the device rotationally stiff, and exerting a counter rotational force in the plantar direction. As the foot rocks forward to the 0 degree equilibrium position, the assistive force is zero. As the foot continues to rock forward toward toe-off, spring 150 is in tension, again making the device rotationally stiff, and exerting a counter rotational force in the dorsal direction. After toe off, the foot again transitions to level (and a zero assistance equilibrium position) before preparation for the next heel strike.

It will be appreciated that by choosing different spring strengths, the magnitude of the dorsi and plantar resisting forces relative to one another can be changed. Additionally, for any pair of spring weights, the equilibrium points can be changed by adjusting the positions of the springs. As is shown at the bottom of FIG. 2 the net torque provided to the footplate by the springs can be stiffened or softened throughout the movement by adjusting the positions of the springs. To take one example, suppose that in the 0 degree position shown in FIG. 1, both springs 145, 150 are under tension, but balanced. In this hypothetical, the equilibrium points for the individual springs would be different, but would be equally disposed on either side of a midline of the pulley, such that both springs are exerting equal and opposite force when the footplate is level. As the user moves from stance to toe-off, the user experiences increasing resistance to plantar extension from the elongation of spring 150, and at the same time, decreasing assistance from spring 145 as it compresses. Thus, the resistance (and therefore the assistance that will be provided to return the foot to level after toe-off), increases with the angle of the movement. The same would be true in the opposite direction. During dorsi extension (called dorsi-flexion in FIG. 2), which is rotating the foot up in preparation for heel strike, spring 145 provides resistance as the foot it rotated up from equilibrium. At the same time, spring 150 compresses and provides less assistance. This stiffening response is reflected in the "stiffening response" curve in FIG. 2. A softening response throughout the movement can be achieved by changing the relative equilibrium angles associated with the springs, such that the assistive spring becomes engaged, for example, at larger angles.

Figure 3:
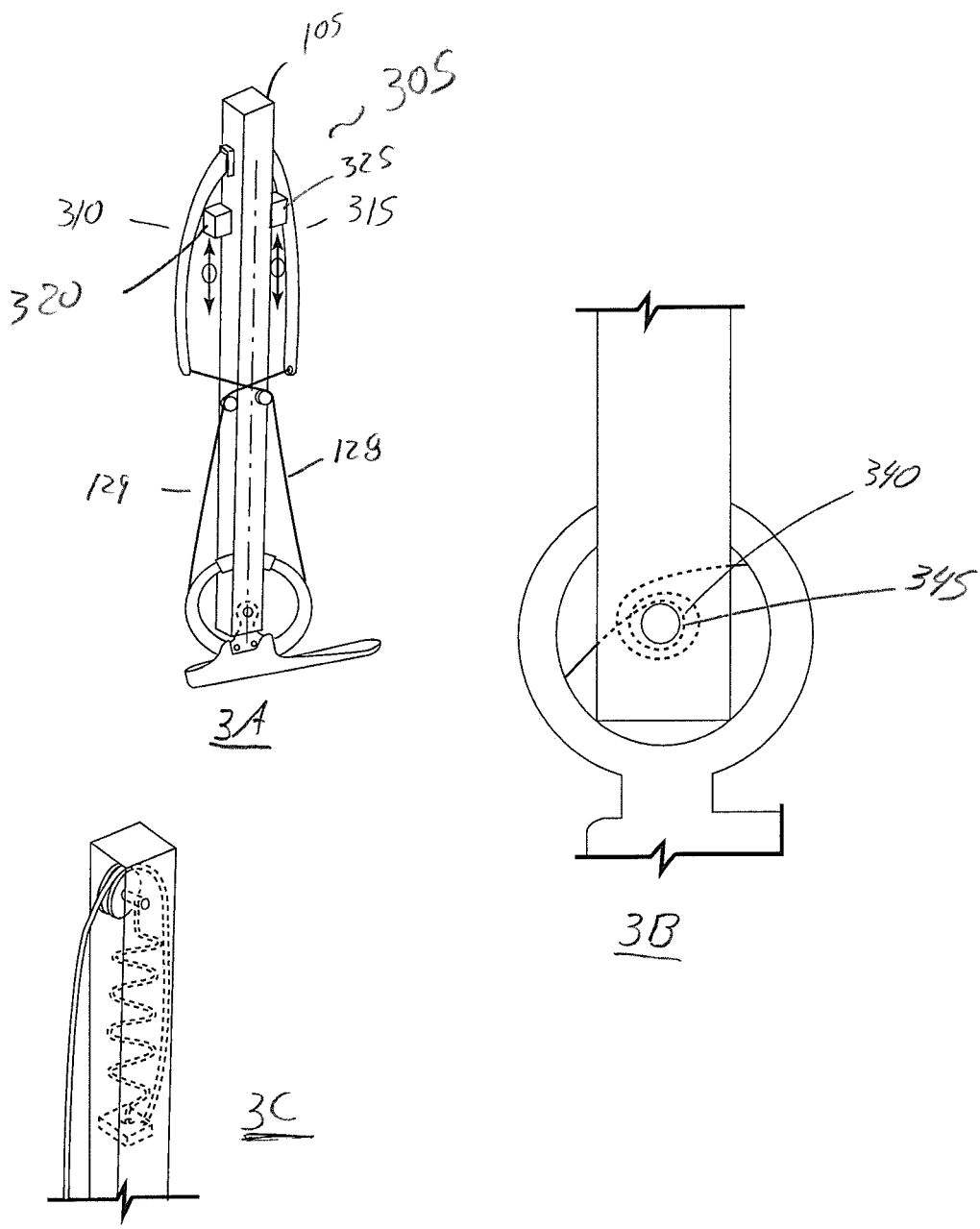
FIG. 3 depicts different spring designs: leaf (3A), internal compression (3C), and rotary (3B).

Alternative arrangements using different sorts of tensioning mechanisms are depicted schematically at FIG. 3. FIG.

3A shows a first alternative AFO 305. In AFO 305, a pair of vertically mounted leaf springs 310, 315 are arranged on a front and back side of member 105. Springs 310, 315 ride on respective pivots 320, 325. Pivots 320, 325 may be fixed, but preferably are slidingly attached to the front and back sides of member 105, for example, in a vertically arranged track, by a rack-and-pinion arrangement, or the like. In such arrangements, pivots may be slid vertically along member 105 and fixed in place. In alternative embodiments, pivots 320, 325 are attachable to member 105 at a variety of discrete or a continuum of fixed positions, by fasteners or the like. Preferably, pivots 320, 325 are independently adjustable. In certain embodiments, pivots 320, 325 are rollers or domes, preferably of some low friction material like polymer. Pivots 320, 325 may be manually adjustable, or translatable by some motorized means. As pivots 320, 325 are translated upward along member 105 toward the fixed connection between springs 310, 315 and member 105, the springs deflect outward from the member, and the free length of the springs shortens, which increases the spring strength. It is contemplated that these various effects will be achieved by the user (or the user's clinical team) by varying the vertical mounting points of the springs, where preferably, the springs themselves (i.e., the spring weights) remain constant. That is to say, this adjustability is accomplished without changing out springs.

Distal ends of springs 310, 315 are connected to tensile force transmitting means 128, 129 (e.g., a cable or chain), via pulleys arranged on or in member 105, to exert pulling force on pulley 125. The cables are routed to engage the distal ends of their respective leaf springs at close to 90 degrees, and preferably, are routed through member 105 (through apertures) to engage pulley 125 on the opposite side. Routing pulleys, as shown, may be provided to accomplish this cable routing. In certain embodiments, routing pulleys are mounted on rotational bearings arranged in the front and back walls of member 105.

FIG. 3B schematically illustrates an alternative embodiment in which a pair of rotary springs 340, 345, are provided that provide counter rotational force at the pulley 125. In cases such as that of FIG. 3B, the rotational springs 340, 345 may be mounted internal to member 105 and medially and laterally on the rotational bearing, for example, on either side of pulley 125. A reinforced ledge or other stopping structure may be provided on the interior of member 105 for the rotational springs to push against as they are loaded. In certain alternative embodiments, this stop may be rotatable, and in some cases, ratcheting, to preload each spring and to change the equilibrium angle associated with each spring. Alternatively, the springs themselves may be rotated with respect to fixed stops.

In an alternative embodiment of FIG. 3B, there is a single rotary spring that is compressed by angular motion in a first direction and extended by angular motion in a second direction. In such cases, there may be one or more adjustable stop surfaces that determine the angle at which the spring starts compressing and the angle at which it starts extending.

FIG. 3C schematically illustrates yet another alternative arrangement using one of more springs that is loaded in compression. The compression spring arrangement of FIG. 3C has the advantage that a single spring may be used, where the spring is connected to both force transmission cables 126, 127, such that compression of the spring provides counter-rotational assistance as the footplate is rotated in either direction. In alternative embodiment, a second spring, which may be a compression spring, is provided for rotation in the other direction.

Combinations of one or more of the spring arrangements depicted in FIGS. 1 and 3 are contemplated and within the scope of the invention.

Figure 4:
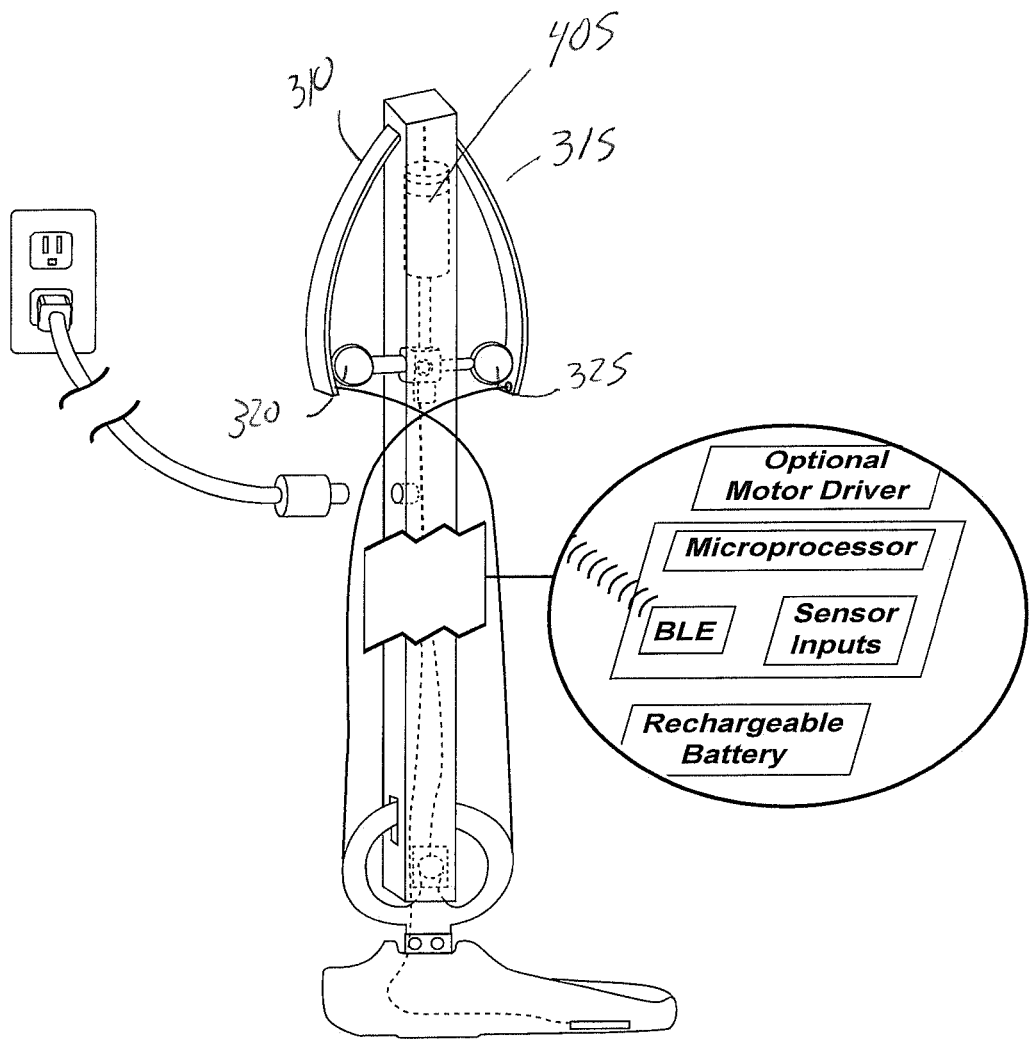
FIG. 4 depicts intelligent AFO components (microprocessor, battery, connectivity, sensors) and optional DC motor for adjusting leaf spring stiffness.

FIG. 4 schematically depicts an alternative embodiment of an AFO according to the invention. The embodiment of FIG. 4 is similar to the embodiment of FIG. 3A in that it uses vertically mounted leaf springs (310, 315) and adjustable pivots (320, 325). However, in the example of FIG. 4, a drive mechanism 405 is provided which can translate the pivots 320, 325 vertically along member 105, thereby adjusting the leaf spring tension, and the amount of torque delivered to the pulley. Such an arrangement is useful for allowing the user to choose the level of stiffness that the AFO provides. In one aspect, drive mechanism includes an actuator such as a DC motor that drives a ball screw in a first or second direction, thereby translating a ball nut. The ball nut is connected by lateral projections to the pivots 320, 325. The lateral projections pass through slots in the front and back surfaces of member 105, and the ball nut may be prevented from rotating with the screw by contact between the lateral projections and the slot's perimeter. Thus, as the screw rotates the ball nut, and therefore the pivots, translate up and down. Other drive mechanisms capable of reversible linear translation are possible, such as cable and pulley, chain and sprocket or rack and pinion arrangements.

In alternative embodiments, each pivot 320, 325 is independently vertically translatable, either manually or through one or more of the drive mechanisms mentioned above. In the case of a mechanized system, this may be accomplished by providing two separate motors. Alternatively, in cases where dynamic or real time adjustability is not a concern, the mechanism that transmits force from the motor to each pivot may be selectable, such that it can selectively translate one pivot, then another. As is discussed above in relation to FIG. 3, having independently adjustable pivots allows the tension being supplied to the pulley by the springs be independently adjustable. This allows the resistance during toe-up and toe-down movements to be independently set.

Drive mechanism 405 may be in electronic communication with drive electronics, which are also shown in FIG. 4. Drive electronics may include a motor driver, which receives control signals from a manual switch or a microprocessor/microcontroller. Motor driver may be powered by a rechargeable battery. Drive electronics may also include a microprocessor or microcontroller in communication with a data transceiver, such as a WiFi or Bluetooth or BLE transceiver. Microprocessor/microcontroller may also be in communication with one or sensors. Sensors may include one or more sensors that provide data on the angular position of the pulley, for example, Hall Effect sensors, IMU, angle encoders or potentiometers. Additional sensors may include accelerometers and gyroscopic or other sensors for detecting angular acceleration. Such sensors may be arranged to gather data regarding the acceleration of the AFO as a whole, for example, to determine its position in the gait cycle. Specifically, such sensors may detect heel strike (from rapid deceleration of the AFO) or swing. Such sensors may be usable to determine whether the user is walking or running, for example, based on the magnitude of the detected accelerations or the frequency of sensed heel strikes. Sensors may also include a pressure sensor, like a force sensitive resistor, located on the footplate under the distal portion of a user's foot, which may gather data reflecting the pressure being exerted by the user on the footplate.

Figure 5:
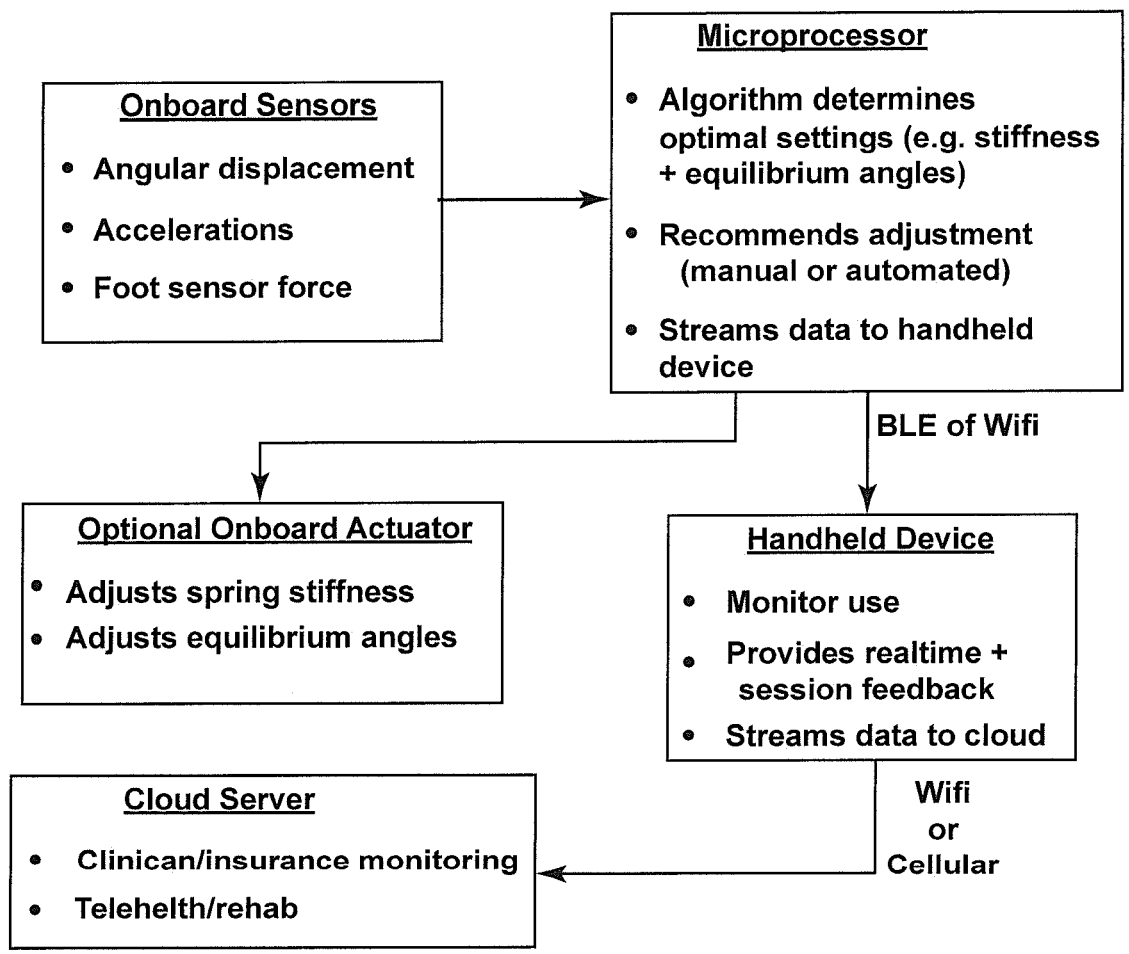
FIG. 5 is schematic depiction of data flow for an intelligent AFO design.

FIG. 5 is a data flow diagram showing, schematically, the operation of the electronic system described above. Onboard sensors may collect use data, which may include data relating to foot pressure, angular displacement of the pulley and/or footplate, and/or angular velocity and acceleration of the pulley or footplate. Additionally, various accelerations may be measured, for example, the angular or linear acceleration of the member 105 or some other part of the AFO. Sensor data is provided to an onboard microprocessor, which analyzes and processes the provided data to generate data about the performance of the device and the activity of the user. For example, the intelligent orthosis system described here may track the number of movements the user performs in a session or over time. For lower-extremity embodiments, the device may track the number of steps, user walking speed, or joint angles. The device may also record and report performance for rehabilitation progress tracking. The microprocessor may also receive the provided data and determine settings, such as spring stiffness and equilibrium angle, on the basis of the received data.

The device may transmit information external to the device (e.g., to the user) regarding the determined spring stiffness and equilibrium settings, so that the user can perform a user-directed manual or motorized adjustment. Alternatively, a microcontroller can provide control signal to the actuator, which adjusts the pivots in accordance with the determined settings. Alternatively or additionally, the determined settings and/or the raw or processed sensor data can be communicated through the transceiver to external computing device such as a handheld device (in the possession or a user, or member of the user's medical or training team), or a remote server such as a cloud server. Either or both of these external computing devices may do the analysis of the data and determination of the spring settings that is discussed above, rather than the onboard microprocessor. In the case where the orthosis is monitored via handheld device (smart phone or tablet), the device may encourage use, provide cues, or use gamification techniques. Either or both of the handheld or cloud server devices may transmit adjustment commands to the microprocessor. As an alternative to direct communication (e.g., over WiFi) between the microprocessor and the cloud server, the handheld device may communicate data to the cloud server, acting as a conduit between the AFO and the cloud server.

For quasi-powered and intelligent configurations as described above, the onboard microprocessor or a remote, connected device, may instruct the onboard actuator(s) to adjust the stiffnesses or equilibrium angles of the spring components. The onboard actuator(s) would then perform the adjustment. The adjustments would be based on a computer algorithm that determines the optimal stiffnesses or equilibrium angles for a given ambulatory condition or speed (e.g., incline, decline, stairs, slow, fast, walking running) based on a foot sensor, angle sensor, accelerometer, or inclinometer in isolation or in combination.

Figure 6:
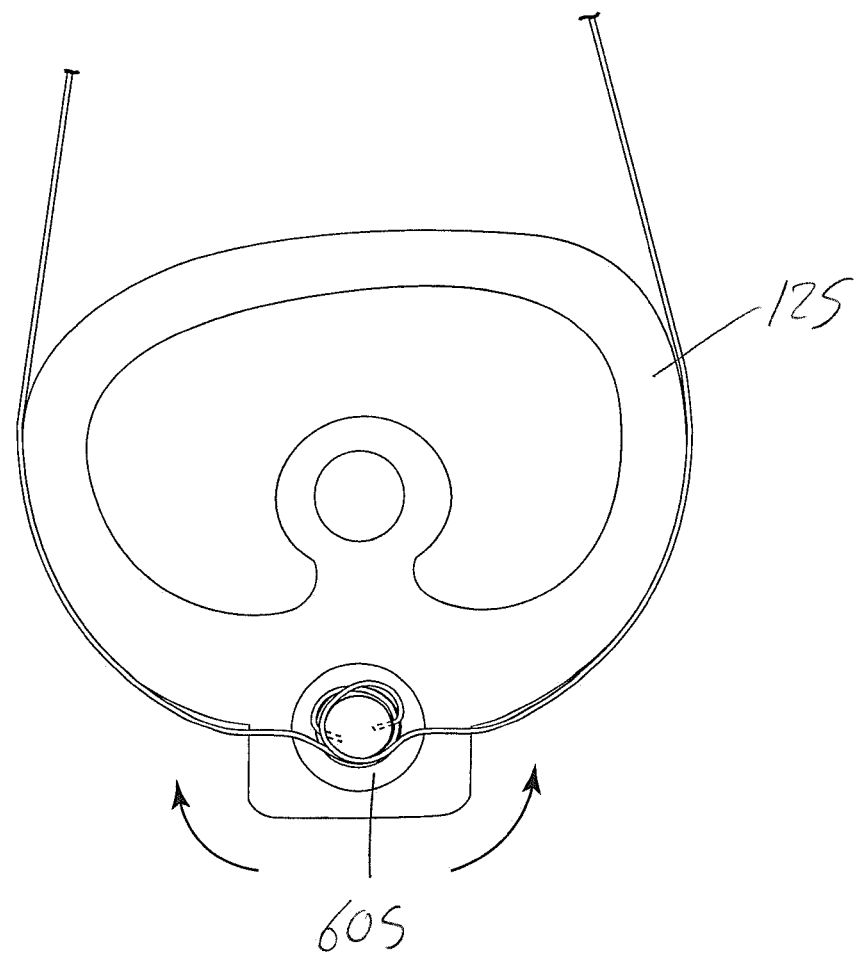
FIG. 6 depicts a manual adjustment knob mounted to the main hinge pulley that adjusts equilibrium angle.

In embodiments, the AFO includes features allowing for quick, manual adjustment (or fine tuning) to the flexion and extension equilibrium angle through turning a knob, adjusting a slider, lever, or other similar mechanism, without the need of hand or power tools. In one example configuration, turning a knob in one direction would tension the cable that attaches to the flexion-resisting spring at the same time, and by the same amount, as loosening the tension to the cable that attaches to the extension-resisting spring; turning the knob in the other direction would have the opposite effect. FIG. 6, for example, shows a pulley 125 having a knob, hub, barrel or sprocket 605, which is selectably rotatable and then rotationally fixable with respect to pulley 125. Distal ends of the transmitting means (e.g., cables) are wound around the knob in opposite directions, and fixed to knob 605. Rotation of the knob creates slack in one cable, while increasing the tension in the other cable. This allows for easy adjustment of the equilibrium angle of the footplate attached to the pulley 125. In certain alternative embodiments, a pair of knobs are provided, around each of which is would one of the cables. In such embodiments, the slack or each cable can be adjusted independently.

Figure 7A:
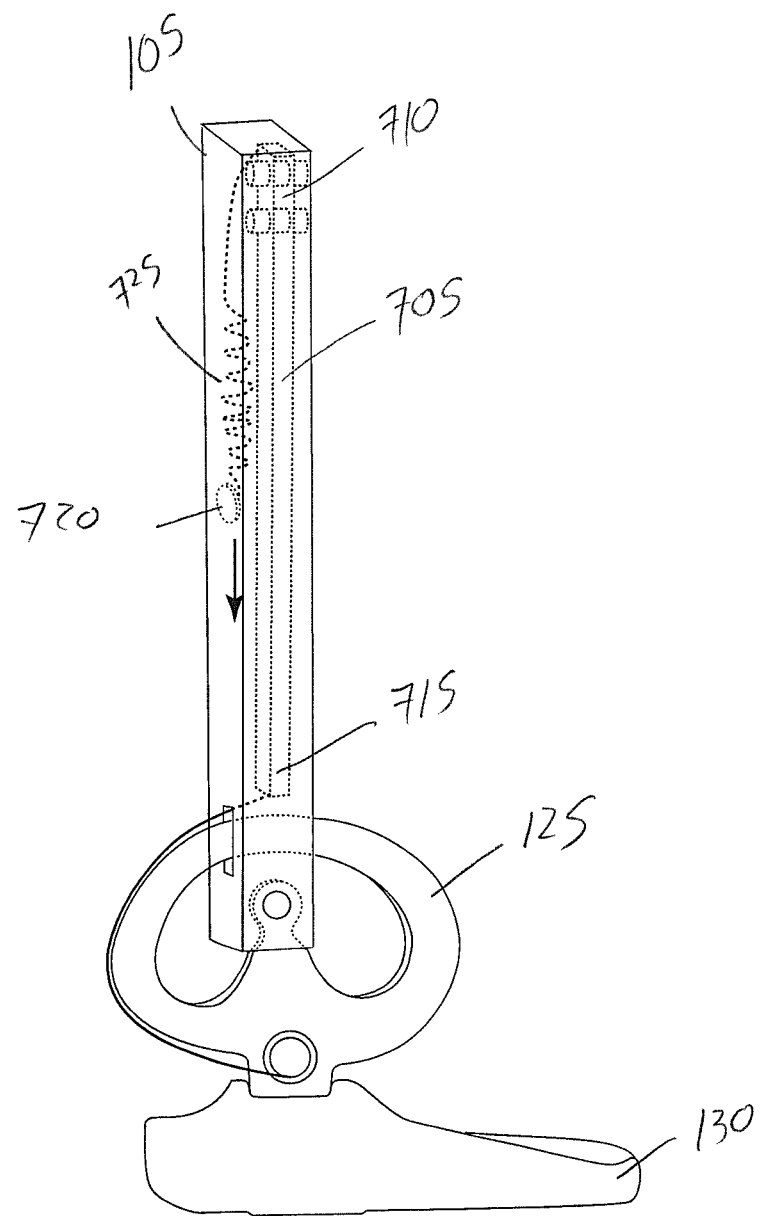
FIG. 7A depicts a passive spring-based mechanism for dynamic leaf spring pivot adjustment.

While the leaf spring embodiments described above in reference to FIGS. 3 and 3A and 4 contemplate externally mounted leaf springs, this is not a requirement. FIG. 7A shows a variable stiffness AFO having a leaf spring that is internal to the tubular upright member 105. The AFO of FIG. 7A, like those discussed above, has a hollow, tubular upright member 105. A stiffening component, in the case of FIG. 7A, a leaf spring 705 is located within the member 105, and is fixedly or adjustably mounted to an interior surface of member at a proximal or first end 710. A distal end 715 of leaf spring 705 is attached to a force transmission mechanism (e.g., a cable, chain, etc.), which is attached to pulley 125. The leaf spring 705, when deflected from its equilibrium position, pulls on the cable, exerting rotational force on the pulley 125 tending to rotate the attached footplate 130 in a downward or plantar extension direction. Thus, the footplate is rotated up, in dorsi extension as during a preparation for heel strike, the cable flexes the leaf spring, which exerts a resistive force on the pulley, which will tend to return the foot plate to a level position. This stiffens the device during the toe-up, heel-down movement. Flipping the orientation of the leaf spring, the direction of the cable, and the attachment point on the pulley reverses the application of the spring force, creating resistance when the footplate is rotated down. A pair of leaf springs, arranged on opposite interior walls (i.e., front and back walls) of the tubular member may be used to provide stiffening during rotation in both directions.

The extent of the stiffening provided by leaf spring 705 may be adjusted by vertical movement of a translatable pivot 720 on which leaf spring 705 rides. Moving the pivot 720 up lengthens the free distal portion of the leaf spring, thereby making it less stiff, while moving the pivot down shortens the leaf spring's free distal portion, thereby making it more stiff. In one embodiment, the vertical position of pivot 720 may be manually adjusted to vary the amount of stiffness imparted to the AFO by the leaf spring. Alternatively, a mechanized means for adjusting the position of the pivot may be provided, such as those discussed above in reference to FIG. 4.

Thus far, embodiments that are manually adjustable and adjustable via a motorized actuator have been described. The embodiment of FIG. 7, however, provides for a fully-passive (i.e., not powered) but dynamic leaf spring pivot point adjustment. The dynamic pivot point adjustment mechanism may incorporate a mass-spring system that changes position based on the motion of the user. For example, in a lower-extremity configuration, the mass-spring system may extend downward upon heel-strike, lowering the pivot point and automatically adjusting the leaf spring stiffness. Larger accelerations caused by more-forceful heel-strikes (e.g., caused by running) would extend the pivot point downward to increase leaf spring stiffness.

In this alternative embodiment, including optional components also illustrated in FIG. 7A, the AFO can be dynamically adjusted in terms of stiffness without the need for a mechanized or active driving mechanism like a motor. Such embodiments are useful for providing variable levels of assistance or resistance to the user, for example, during different stages of the gait cycle, or when the user is engaged in running versus walking. In an alternative embodiment, pivot 720 is attached to a spring 725, which exerts upward force on pivot 720, tending to translate pivot 720 in an upward direction until the spring force is balanced by the weight of the pivot. During a heel strike, the AFO (including the spring mounting point) experiences a sudden deceleration of its velocity in the downward direction. The AFO stops suddenly, but the pivot continues to move down, momentarily overcoming the spring force. In its new position, the pivot effectively shortens the free end of the leaf spring, increasing its strength and the resulting resistance it provides to certain ankle movements (in the case of FIG. 7A, the resistance to plantar extension movements is increased).

Figure 7B:
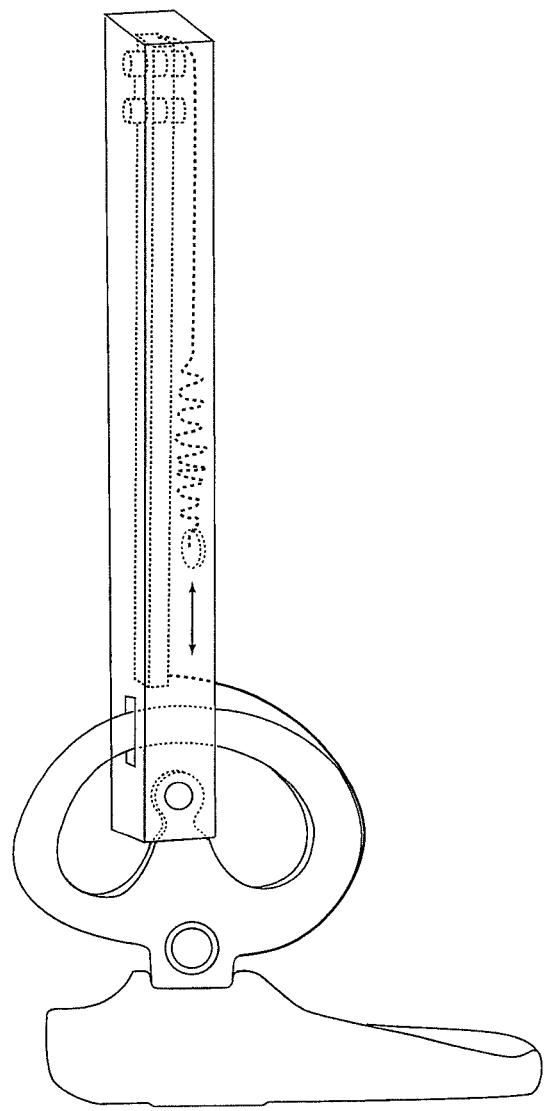
FIG. 7B depicts a passive spring-based mechanism for dynamic leaf spring pivot adjustment having a different orientation.

FIG. 7A illustrates a single leaf spring creating resistance to dorsi extension, and having a pivot point that can be dynamically adjusted upward and downward through the use of the device. It is contemplated that the mechanism shown in FIG. 7A can flipped, so that it provides resistance to plantar extension. Such an embodiment is illustrated in FIG. 7B. In this embodiment, the leaf spring is mounted to a back (posterior) wall of the tubular member, where in the FIG. 7A embodiment, a single spring is mounted to the front (anterior) wall of the tubular member. In the FIG. 7B embodiment, at heel strike, the pivot moves down by the sudden deceleration of the AFO. As the user moves through mid-stance to toe-off, the heel comes up, and footplate rotates down. This pulls against the leaf spring which is now shortened against the pivot, so it is stiffer. During swing, the foot rotates back to level, assisted by the stored energy in the spring, and then to toe-up in preparation for the next heel strike. As this happens, the leaf spring is relaxing, and pivot will tend to translate up, softening the assistance.

It should be appreciated that both mechanisms depicted in FIGS. 7A and 7B may be combined in the same AFO, similar to the arrangement depicted in FIG. 3A, but with the leaf springs internal to the tubular member.

Figure 8:
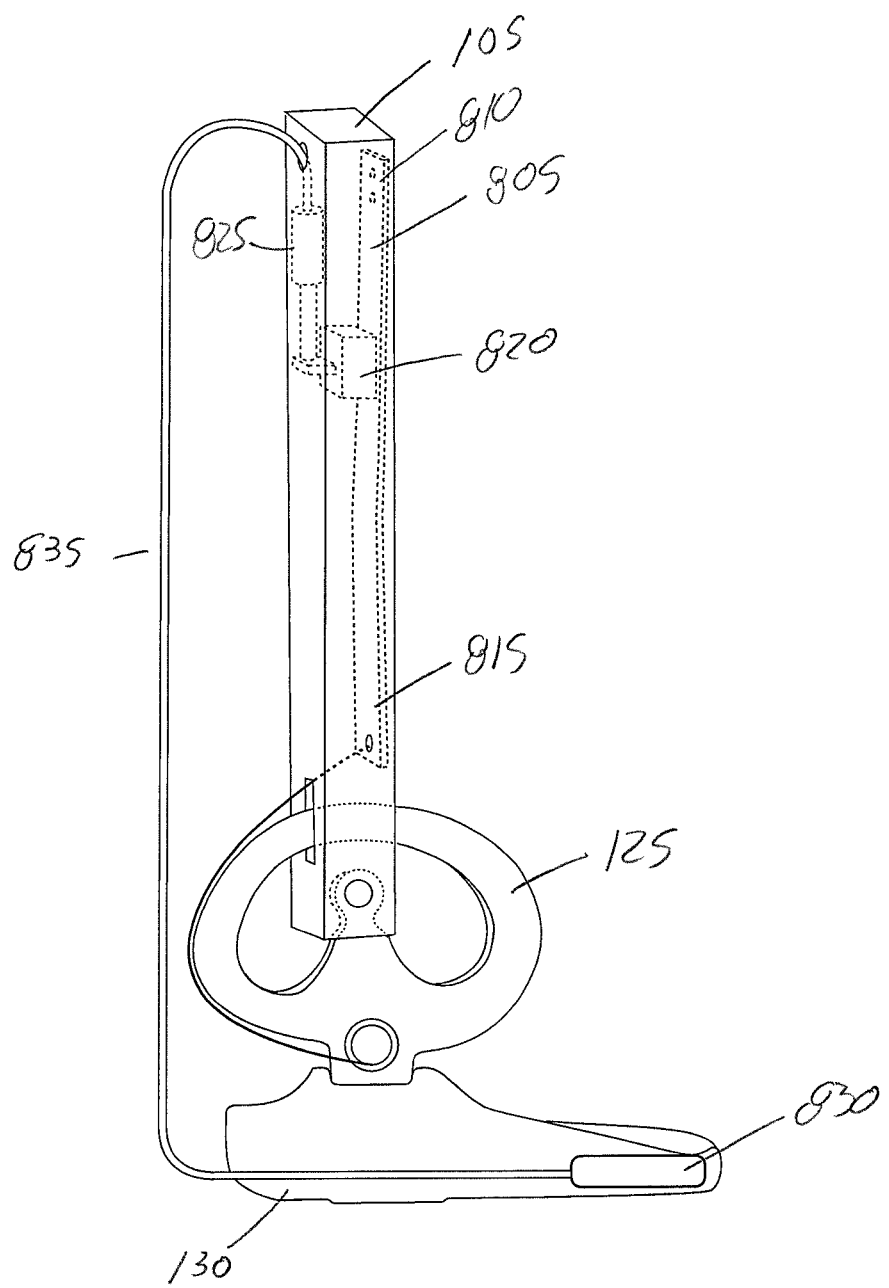
FIG. 8 depicts a hydraulic-piston-based mechanism for dynamic leaf spring pivot adjustment.

Another passive yet dynamic mechanism for adjusting leaf spring pivot point position includes a hydraulic system to transfer pressure from under the foot to a linear slider (or similar) that actuates the pivot point. FIG. 8 illustrates such an alternative dynamic AFO with variable resistance/assistance. In the embodiment of FIG. 8, like that of FIG. 7, a stiffening component, in the case of FIG. 8, a leaf spring 805 is located within the member 105, and is fixedly or adjustably mounted to an interior surface of member at a proximal or first end 810. A distal end 815 of leaf spring 805 is attached to a tensile force transmission mechanism (e.g., a cable, chain, etc.), which is attached to pulley 125. The leaf spring 805, when deflected from its equilibrium position, pulls on the cable, exerting rotational force on the pulley 125 tending to rotate the attached footplate 130 in a downward or plantar extension direction. Thus, in one configuration, when the footplate is rotated up, in dorsi extension as during a preparation for heel strike, the cable flexes the leaf spring, which exerts a resistive force on the pulley, which will tend to return the foot plate to a level position. This stiffens the device during the toe-up, heel-down movement. Flipping the orientation of the leaf spring, the direction of the cable, and the attachment point on the pulley reverses the application of the spring force, creating resistance when the footplate is rotated down. A pair of leaf springs, arranged on opposite interior walls (i.e., front and back walls) of the tubular member may be used to provide stiffening during rotation in both directions.

The embodiment of FIG. 8 includes a vertically moveable pivot 820, which translates vertically within member 105. As with the pivot in the FIG. 7 embodiments, locating the pivot closer to the distal end of leaf spring 805 makes it stiffer, and locating the pivot closer to the proximal end makes it stiffer. Pivot 820 may be translated down by an attached piston, which is part of hydraulic assembly 825. Hydraulic assembly 825 is connected via hydraulic fluid line 835 to a compressible hydraulic bladder 830. When bladder 830 is compressed, hydraulic pressure is transmitted to the hydraulic assembly, which actuates the piston, causing the pivot to translate in a downward vertical direction. The pivot can be retracted in the vertical direction by the relaxation of hydraulic pressure, which will occur when bladder 830 is no longer compressed. A non-illustrated spring may be included to assist in the vertical translation of pivot 820.

In operation, when a user applies downward pressure to the footplate 130, the bladder is compressed causing the pivot to move downward, shortening the free end of leaf spring 805. This will tend to stiffen the spring and increase resistance during toe-down movements, like the transition to terminal stance, right before toe-off. As the foot comes up, the hydraulic pressure drops, and the pivot translates up, weakening the spring, which then provides less resistance to two-up movement, as before heel strike.

As with FIG. 7, it is contemplated that the leaf spring orientation and the position of the pivot can be flipped, and that two assemblies can be provided, on each of the front and back walls of the member 105 to provide assistance/resistance in both angular directions.

Throughout this disclosure AFO's have been described in the context of unilateral devices for one ankle, however, this is not a requirement. It is contemplated that pairs of devices such those described herein will be used, one for each ankle of a user, and such devices are squarely within the scope of the invention.

Thus far, the present disclosure has been directed to assistive devices, described in reference to exemplary AFOs, which use spring elements to store energy created by a user's ankle/foot movements during certain stages of the gait. The spring elements then return this stored energy to the user in the form of assistive torque during certain stages of the gait. The springs can be positioned to undergo tensioning at various different stages of the angular rotation of the pulley/footplate. The springs can also be positioned such that they work against each other, to various degrees, at various different stages of the angular rotation of the pulley/footplate. This permits the applied torque curves to be tuned to create, for example, softening or stiffening resistance (or weakening or strengthening of assistance) at different stages of the angular rotation of the pulley/footplate. The concepts described thus far described allow for the design of passive (i.e., non-motorized) devices, and for devices where the role of actuators is limited to changing the strength of the springs.

In other embodiments, the concepts here before described are applied to active exoskeletal AFOs. Active AFOs generally use one or more actuators, such as motors, to apply assistive torque to a joint of the user during various stages of a gait cycle. These devices may also provide resistive torque. Generally, an active AFO will have a pair of wearable, battery powered, counter-rotating motors, one for each limb, each motor connected to a pair of force transmitting linkages (preferably Bowden cables). Each pair of Bowden cables is connected to a pulley, which is connected to a footplate. When a motor rotates in one direction, the footplate rotates in a toe-up direction, and when the motor rotates in the opposite direction, the footplate rotates in a toe down direction. This applied assistive torque assists a user with walking. Again, these devices may be configured to provide resistance rather than assistance. An exemplary powered AFO is described in U.S. Patent Publication No. 20190343710, entitled EXOSKELETON DEVICE, the entirety of which is incorporated herein by reference.

The passive spring-based energy storage concepts outlined above may be combined with a powered exoskeletal AFO, in a parallel configuration, to combine active (i.e., actuated) and passive (i.e., spring-assisted) components to improve the performance of either component independently. Such devices may use springs having adjustable stiffness, to allow the devices to be tuned to each user's preferences, needs or body mass. When configured I parallel to the powered actuation system, the spring components can offload motor requirements to result in a lighter weight exoskeleton design, save battery capacity, and/or increase battery life. Additionally, the spring can increase the amount of torque and positive powered force provided to the user at very low cost and low added mass.

In one embodiment, a powered ankle exoskeleton is provided, which provides plantar-flexor and/or dorsi-flexor assistance during walking or running. During certain phases of the gait cycle, like stance phase, a parallel leaf spring coupled to the pulley engages (stores and returns elastic energy as the lower-limb naturally dorsi-flexes), which offloads assistive torque and/or power output requirements from the motor. This leaf spring design allows for change in stiffness by changing the leaf spring and also a rapidly adjustable pivot point, which changes the spring stiffness without replacement so that it can be customized to each user, their body mass, or ambulatory condition (e.g., slow walking, fast walking, running). In another embodiment, the exoskeleton is used to provide resistance during walking or running, and the leaf spring is engaged in an opposite direction (off-loading the required resistive torque and/or power output from the motor).

Figure 9:
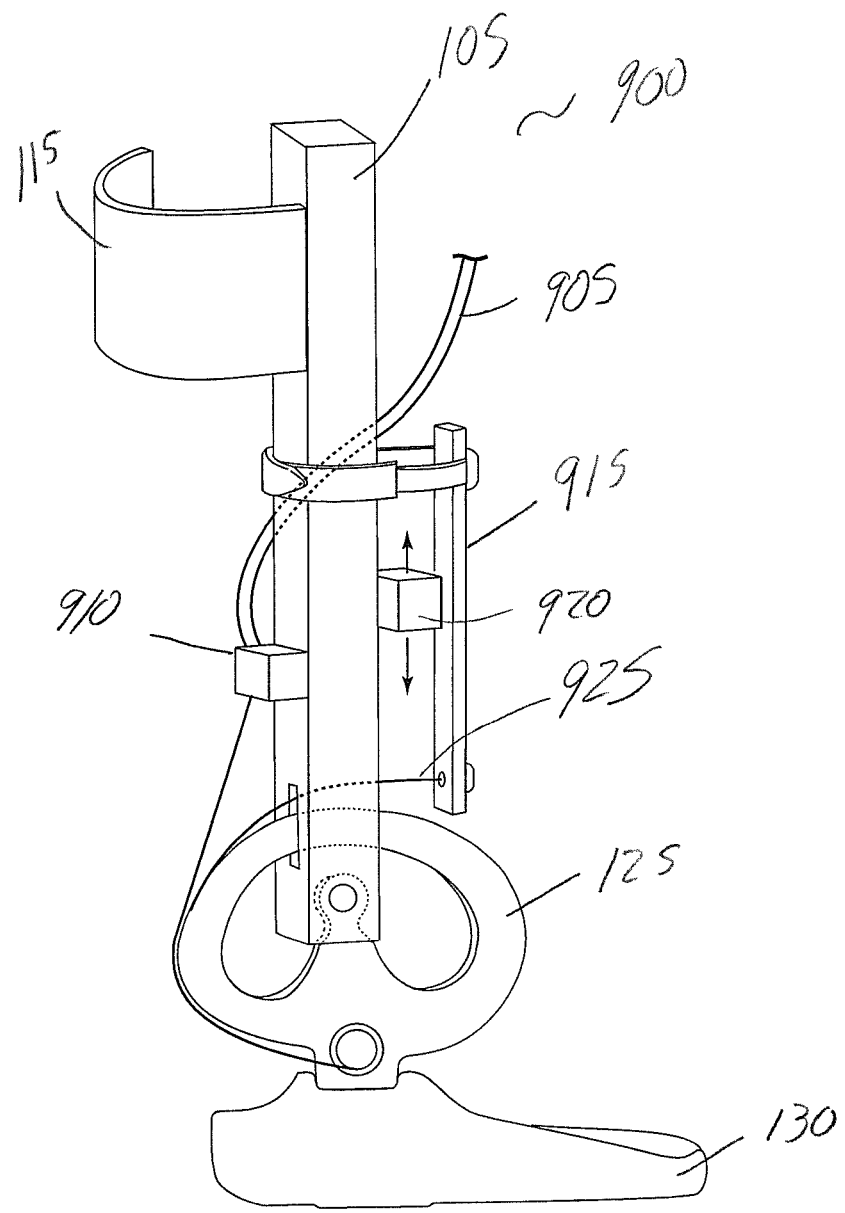
FIG. 9 depicts a powered AFO with a parallel mounted spring for additional assistance.

One such example incorporating the concepts outlined above is depicted in FIG. 9. There is shown the lower portion of an AFO 900. The AFO has an upright (vertical), tubular member 105 such as those described above. A rotational bearing carries a rotational element such as a pulley 125 within the interior walls of member 105. The pulley 125 is coupled to a footplate 130. A tensile force transmission mechanism (cable, cord, ribbon, chain, etc.), but preferably a Bowden cable 905, has a distal end that is coupled to one side of pulley 125. In the case that mechanism 905 is Bowden cable, the sheath may be anchored at an anchor point 910 on or near member 105, and near pulley 125. The cable 905 has a proximal end that is coupled to a non-illustrated actuator such as a wearable, battery powered motor operable to pull on the cable, and then allow the cable to extend again when subject to pulling force. In the example of FIG. 9, the motor and cable are operable to provide ankle torque in a plantar-extension, or toe-down direction to provide assistance while working, or to provide dorsi extension resistance. The embodiment of FIG. 9 also includes spring 915, which in this example is a leaf spring. Spring 915 is mounted to a wall of member 105 at a top or proximal end. Spring 915 is coupled to a tensile force transmitting mechanism 925 (e.g., a cable), at a bottom or distal end. The cable couples the spring to the pulley. In the configuration as shown, when the user rotates footplate in a toe-up direction (e.g., in preparation for heel strike), spring 915 is tensioned. The stored energy is then released as the spring applies toe-down torque to the pulley/footplate as the user proceeds through mid-stance to toe-off. This provides assistance to that movement, and it reduces the amount of powered torque assistance needed from the motor for the movement.

The device of FIG. 9 also includes a pivot 920, which may be adjusted in terms of its position so that it may contact the leaf spring 915 at variable positions along its length. The pivot may be slid and secured by the user manually, or it may be moved by an actuator as set forth in the embodiments above. The positioning of the pivot may be the user's decision, or it may be determined automatically, for example, in accordance with the methods discussed in reference to FIGS. 4-5. The positioning of the pivot varies the length of the free end of the spring 915, which adjusts the spring's strength.

While the example of FIG. 9 shows a spring providing parallel assistance for a single actuated cable for plantar-extension, other configurations are possible and within the scope of the invention. A device with a pair of actuated cables connected to one or more counter-rotating motors providing both dorsi and plantar extension is contemplated. The use of one or two leaf springs, each for a different rotational direction is also contemplated. Leaf springs that work against the actuated direction, to reduce assistance or otherwise tune the response curve are possible. Any combination or positioning of leaf springs, in combination with any combination or positioning of actuated cables is within the scope of this disclosure.

Figure 10:
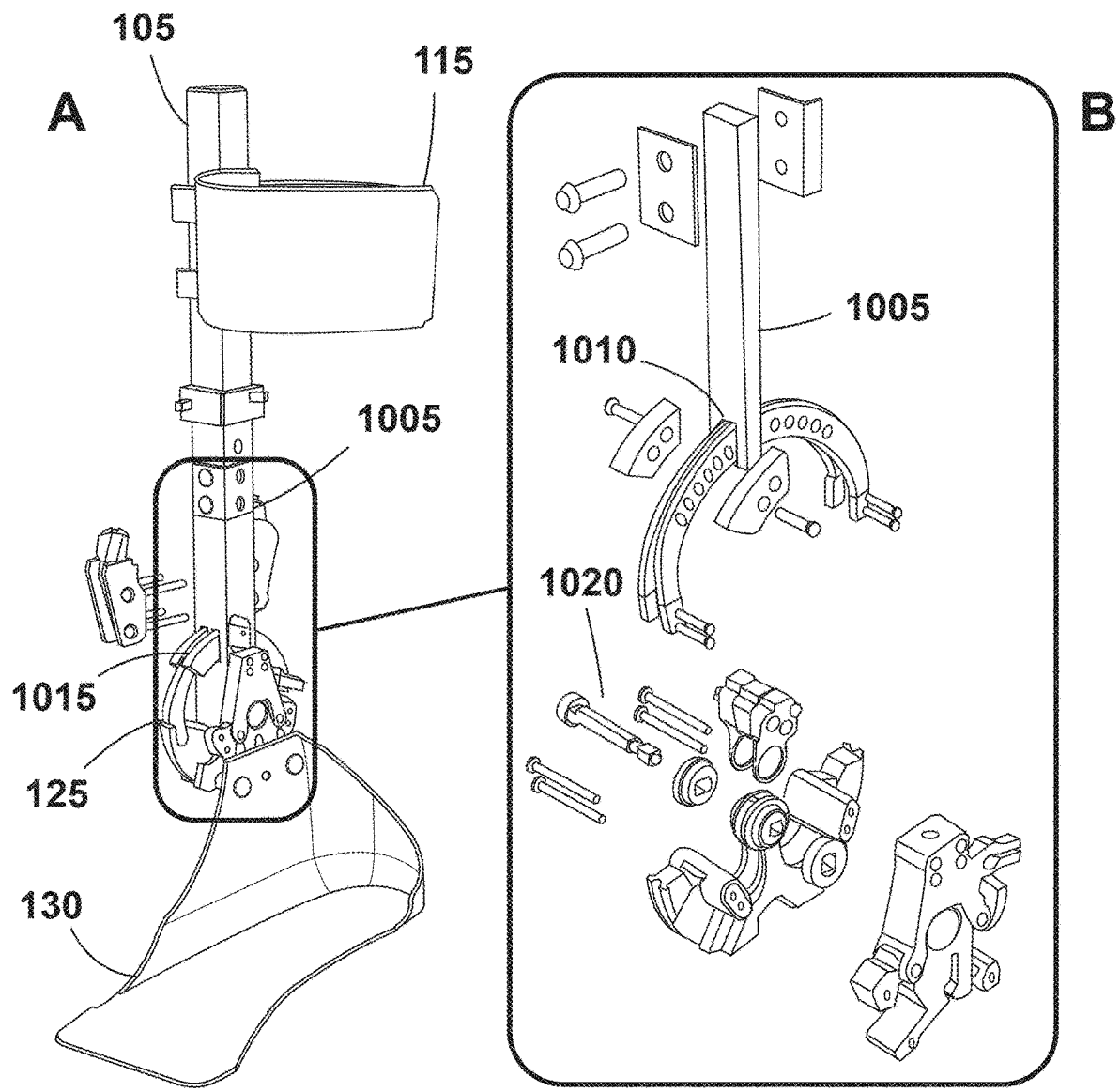
FIG. 10 depicts an alternative embodiment of a powered or passive AFO having an internally mounted leaf spring.

An alternative embodiment of a passive assistive AFO is shown in FIG. 10. The device of FIG. 10 includes a hollow, upright member, again, preferably made of carbon fiber, and a medially projecting user attachment device 115, such as a calf cuff. Inside the member is mounted a vertically arranged leaf spring 1005 (e.g., an elastic carbon fiber bar), which is mounted at a proximal end to an inside wall of member 105. Mounting can be done with a stand-off block ("1"), a cover ("3") and fasteners as illustrated in the magnified portion of the figure denoted as "B". The device includes a footplate 130, coupled to a pulley 125, which rotates with a rotational bearing mounted through side walls of the member 105, such that the side surfaces of the pulley are within the member side walls. An upper portion of the pulley 125 is removable (the removable section denoted as "4"), and this portion passes in a slot or aperture in the member 105. The upper portion of the pulley 125 also passes through a slot or aperture in the leaf spring 1005 at position 1010. This slot or aperture has a width that clears the width of the upper portion of the pulley, but does span the entire width of the anterior and posterior surfaces of the spring 1005. This will allow for an interference to occur between stops 1015 (also denoted "5" in B) and the leaf spring, as will be discussed below. The pulley 125 includes a rotational bearing that rotates around axle pin 1020, which is secured by and between medial and lateral walls of the member.

In certain embodiments, the components illustrated in FIG. 10 are part of a powered device, where a pair cables, e.g., Bowden cables, are coupled to the pulley to provide powered dorsi and plantar extension assistance. In such cases, these cables will be coupled to a non-illustrated battery powered motor that can provide tension and therefore rotation and counter rotation to the pulley. In these embodiments, the device may include a pair of Bowden cable tensioners (as marked in A) to which the sheaths of the Bowden cables are mounted. The tensioners may include barrels that allow the tension between the sheaths to be varied with respect to the inner cables. In active devices the footplate 130 may be attached to the pulley 125 via an optional strain sensor and mounting block ("8" in B), which may be useful for data collection and computing desired supplied power ankle torque. In alternative passive embodiments, the footplate may mount directly to the pulley without an intervening sensor block. Active or passive devices may also include other sensors, such as an angle encoder ("6" in B) or other angle position, velocity, or acceleration sensor, and one or more pressure sensors on the footbed.

In the device of FIG. 10, one or more stop assemblies 1015 may be affixed to the pulley 125 at a variety of positions along the pulley's perimeter. In one case, there are a number of fixed positions the stop assemblies can occupy, but alternatively, the stop assemblies could be slid along continuously and fixed at a continuum of positions, using a tensioning mechanism. Fixed positions may be preferable because the stop assemblies must resist a large amount of shearing force in operation. The positions of the stop assemblies along the pulley determine the angular position of the pulley at which the leaf spring 1005 is engaged and deflects. Referring now to stop assembly 1015 in A, as the footplate pictured is rotated into a more toe-up position, the leaf spring will be engaged and will store energy, which will be returned as the foot is rotated back down. Another stop assembly on the anterior side of the leaf spring will perform the same function for toe-down rotation. By adjusting the positions of the stops, the angles at which resistance begins can be changed.

In alternative embodiments, the device of FIG. 10 may include one or more adjustable or fixed pivots arranged within the member 105. These pivots are arranged between the leaf spring and the interior surfaces of the member such that the spring engages the pivot when it deflects in the direction of the pivot. The pivots can be slid up or down the length of the leaf spring, by the user, to change the strength of the spring for a given direction of rotation. A pivot on the anterior side of the spring will stiffen the spring against footplate rotation in a toe-up direction as the pivot moves down. A pivot on the posterior side of the spring will stiffen the spring against footplate rotation in a toe-down direction as the pivot moves down. Both pivots are independently adjustable and fixable by the user.

Figure 11:
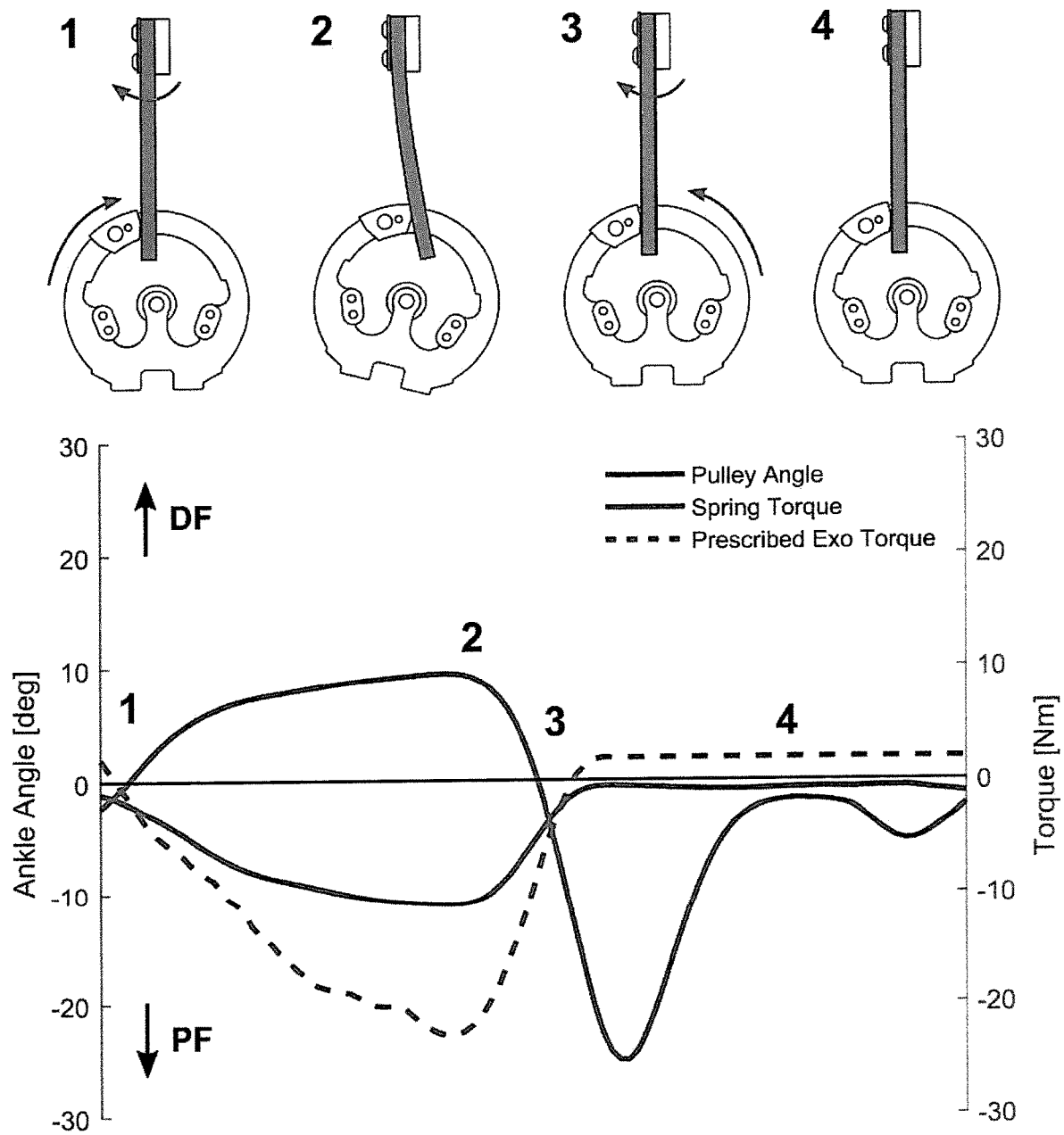
FIG. 11 depicts the operation and torque profile of the embodiment of FIG. 10.

FIG. 11 shows how the device of FIG. 10, in one configuration with a stop assembly placed as shown, will store and return torque to the pulley/footplate thought the stages of the gait. Here, the stop is placed on the anterior side of the pulley and engages the spring upon rotation in the dorsi flexion (toe-up) direction. As can be seen, the spring provides increasing resistance and energy storage during the stance. During the mid to late stance push-off phase, the spring returns the energy as the foot rotates to level, and the spring is not, or is minimally, engaged as the user rotates the foot forward during the swing phase. In the case of an active assistive device, the prescribed assistive torque during these movements may be represented by the dotted line ("prescribed external torque"). As can be seen, the torque curve of the passive spring matches the prescribed torque curve quite well, suggesting that the spring can be helpful in reducing the amount of torque delivered by the motor of the active device, at all gait stages. An engagement clutch may be used to engage the previously described dorsi flexion resistance spring at heel strike and release the dorsi flexion resistance spring at toe-off to allow for unresisted dorsi flexion during the swing phase. As depicted, the motor may need to over power the dorsi flexion resistance spring during swing phase; however there would be a net positive/beneficial effect for the spring offloading the motor across the entire stance phase because the ankle is in greater dorsi flexion during stance phase than during swing phase.

Figure 12:
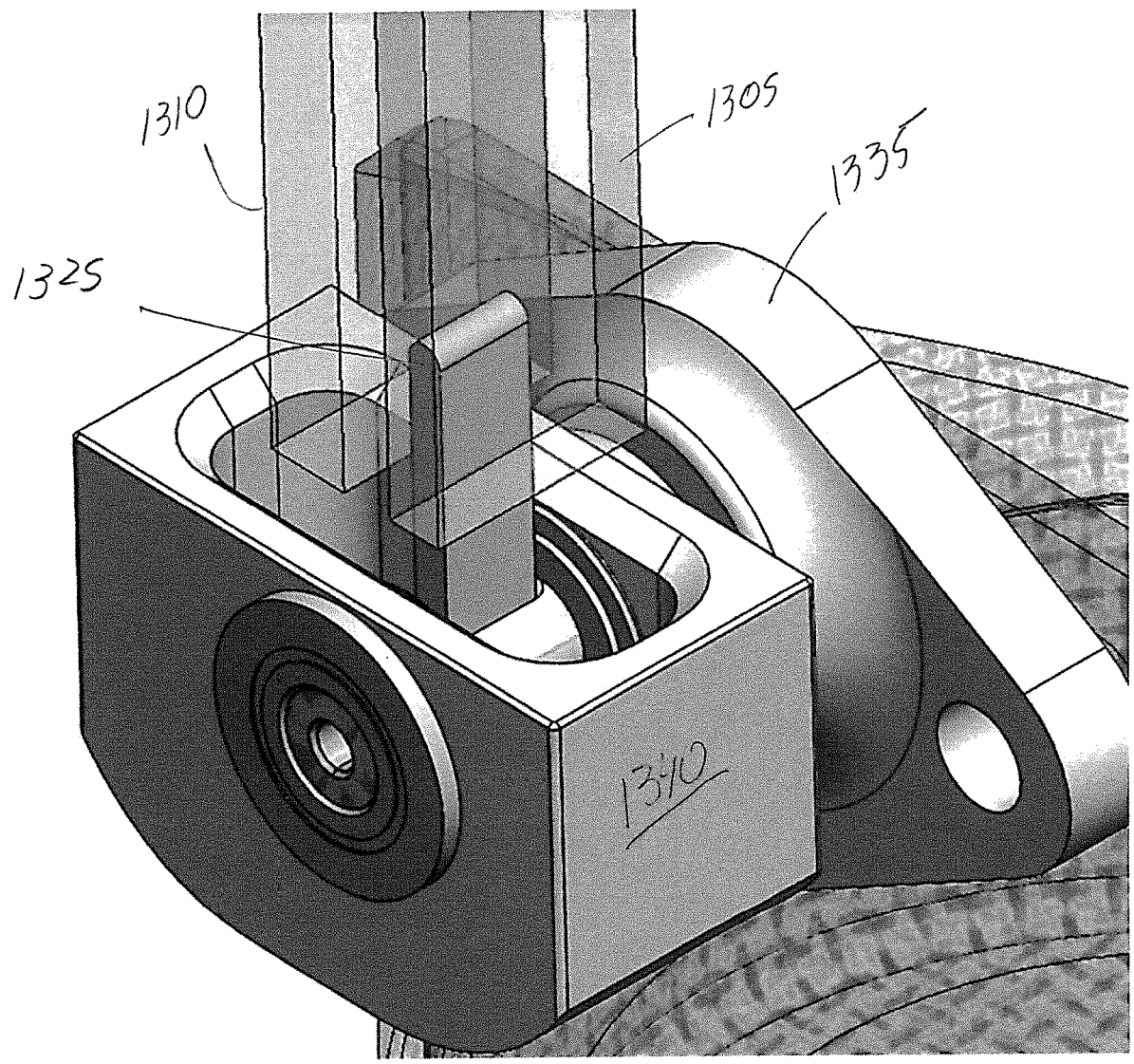
FIG. 12 depicts an AFO having a pair of internally mounted leaf springs.
Figure 13:
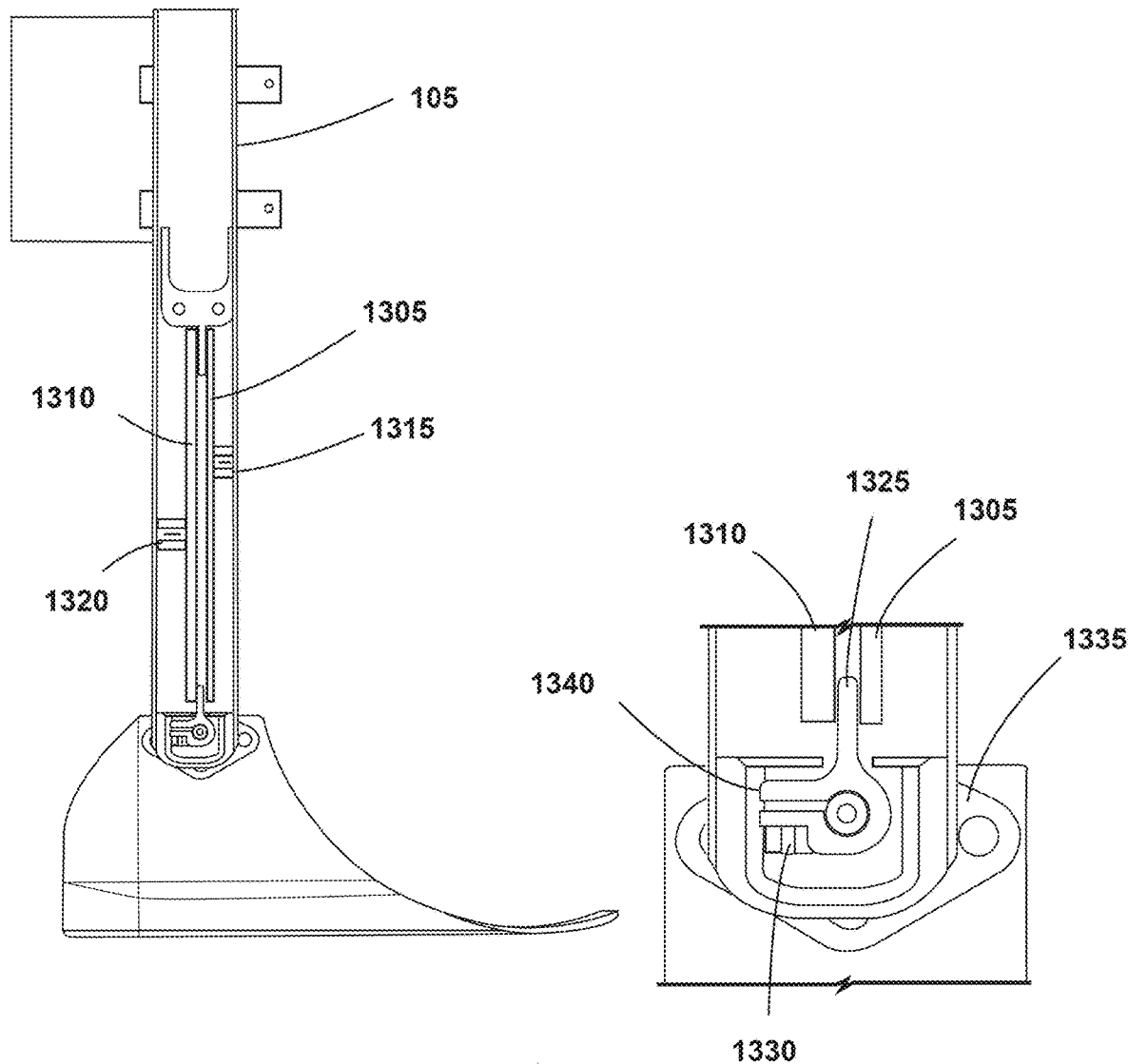
FIG. 13 depicts an alternative view of the passive AFO of FIG. 12.

FIGS. 12 and 13 illustrate an alternative assistive device incorporating a pair of vertically mounted, spaced apart leaf springs, preferably arranged within the hollow upright member of the device. In the arrangement of FIGS. 12 and 13 a posterior spring 1310 and an anterior spring 1305 are arranged on posterior and anterior sides of the upright member 105. These springs are mounted to the member 105 at their proximal ends. The device also includes a pair of spring pivots 1315, 1320, which may be slid vertically between the interior walls of the member and the springs, and fixed in position, where they will be engaged by their respective spring. This allows a user to set the strength of each spring, as in the embodiments described above. A rotational hinge element 1340 includes a bearing, which may receive a non-illustrated axle pin, which is secured by and between the medial and lateral walls of the member, as in the embodiment of FIG. 9. Thus, hinge element 1340 is arranged within the member and rotates with respect to the member. The hinge element 1340 is coupled to a mounting block 1335 (e.g., through an aperture in a medial sidewall of the member), which is coupled to a footplate. Again, this permits the footplate to rotate with respect to the member and the rotational hinge element.

The rotational hinge element 1340 includes a tab or projection 1325 which projects upwardly and is arranged between the distal free ends of the leaf springs. When the footplate rotates in a toe-up direction, the tab engages the anterior leaf spring 1310, and when the footplate rotates in a toe-down direction, the tab engages the posterior leaf spring 1305. In each of these movements, the spring stores energy, and returns it as torque to the footplate when it counter-rotates.

In certain embodiments, the tab 1325 is mounted to the bearing portion of the hinge mechanism 1340 via a clamp 1330. The clamp 1330 may be loosened and retightened to allow the user to change the angle between the tab 1325 and the remainder of the hinge mechanism 1340. This allows angular adjustment to be made between the footplate and the tab, which allows the user to set the equilibrium angle of the footplate, i.e., the angle at which the footplate rests before further motion in either direction engages either spring.

Figure 14:
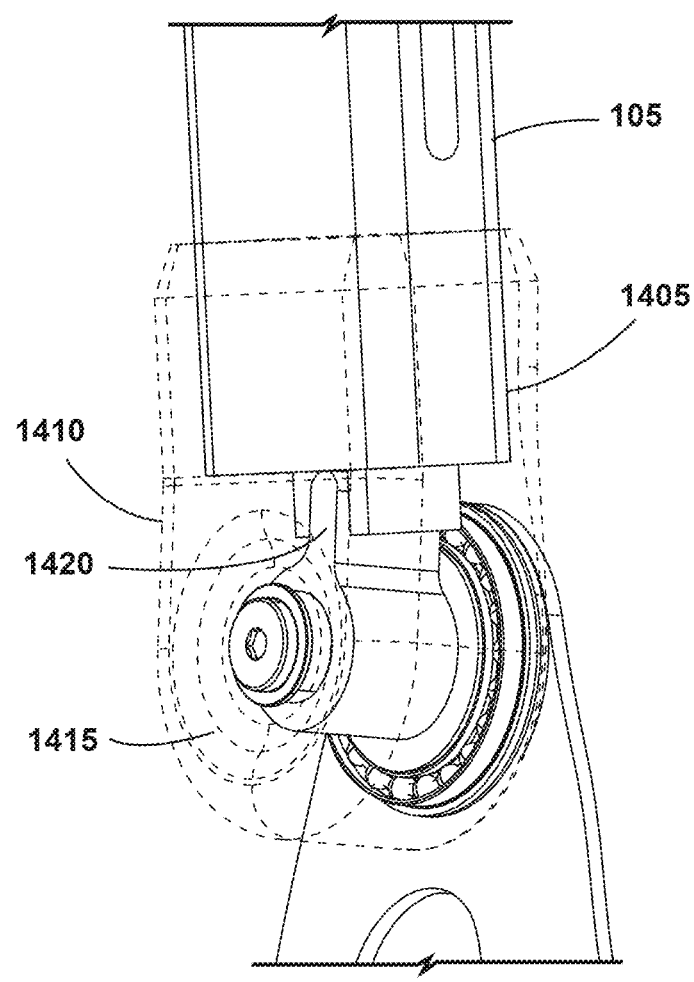
FIG. 14 depicts an equilibrium adjustment mechanism usable with the embodiments described herein.

FIG. 14 shows an alternative arrangement for adjusting the equilibrium angle of the footplate and the spring-engaging tab. In the embodiment of FIG. 14, the distal end of member 105 includes a termination cap 1405, which defines a through aperture. The aperture receives a non-illustrated axle pin. A rotational bearing 1415 is secured within the cap and rotates around the axle pin. The rotational bearing 1415 includes an upwardly extending tap 1420, which extends up between the distal ends of non-illustrated leaf springs. The rotational bearing 1420 has on a medial side teeth, which engage corresponding teeth on an upper tab coupled to the footplate. The footplate tab and the rotational bearing can be held in tension by non-illustrated one or more fasteners such that the two parts rotate with respect to the member together. The fasteners may be loosened, and the relative positions of the rotational bearing and the footplate tab can be changed. This has the effect of changing the angle of the footplate with respect to the tab, which allows for the equilibrium angle of the footplate to be adjusted.

The exemplary embodiments described above have been AFO's or orthoses that provide assistance or resistance to a user's ankle. The personal of ordinary skill will appreciate that the teachings of this disclosure are equally applicable to other joint orthoses such as orthoses for wrists, knees and elbows.

It will be understood by one having ordinary skill in the art that construction of the described invention and other components is not limited to any specific material. Other exemplary examples of the invention disclosed herein may be formed from a wide variety of materials unless described otherwise herein.

For purposes of this disclosure, the term "coupled" (in all of its forms: couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

Furthermore, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected" or "operably coupled" to each other to achieve the desired functionality, and any two components capable of being so associated can also be viewed as being "operably couplable" to each other to achieve the desired functionality. Some examples of operably couplable include, but are not limited to, physically mateable, physically interacting components, wirelessly interactable, wirelessly interacting components, logically interacting, and/or logically interactable components.

It is also important to note that the construction and arrangement of the elements of the invention as shown in the examples are illustrative only. Although only a few examples of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connectors or other elements of the system may be varied, the nature or number of adjustment positions provided between the elements may be varied. It should be noted that the elements and/or assemblies of the system might be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary examples without departing from the spirit of the present innovations.

Reference throughout this specification to "one embodiment," "an embodiment," or similar language means that a particular feature, structure, or characteristic described in connection with the embodiment is included in at least one embodiment. Thus appearances of the phrase "in one embodiment," "in an embodiment," and similar language throughout this specification may, but do not necessarily, all refer to the same embodiment.

The exemplary structures disclosed herein are for illustrative purposes and are not to be construed as limiting. In addition, variations and modifications can be made on the aforementioned structures without departing from the concepts of the present invention and such concepts are intended to be covered by the following claims unless these claims by their language expressly state otherwise.

The invention claimed is:

1. A wearable assistive device, comprising:
    an extended, hollow, tubular structural member having a closed circumferential cross section, a first end and a second end defining a long axis through a center of the extended, hollow, tubular structural member;
    an attachment device coupled to the extended, hollow, tubular structural member and extending medially from the extended, hollow, tubular structural member, the attachment device configured to secure the extended, hollow, tubular structural member to a limb of a user;
    a rotational bearing disposed within the extended, hollow, tubular structural member and positioned on the long axis near the second end of the extended, hollow, tubular structural member;
    a rotational element coupled to the rotational bearing;
    a footplate dimensioned to support a foot of a wearer of the assistive device and coupled to the rotational element such that it may rotate with respect to the long axis of the extended, hollow, tubular structural member;
    a leaf spring attached to the extended, hollow, tubular structural member; and
    a cable having a first end and a second end, the first end coupled to the leaf spring and the second end coupled to the rotational element,
    wherein the rotational bearing is supported on both ends by a first pair of opposing side walls of the extended, hollow, tubular member, and the rotational element includes a portion that passes through apertures having a closed circumference defined in a second pair of opposing side walls of the extended, hollow, tubular structural member.

2. The device of claim 1, wherein the rotational element is one of a pulley, cam pulley or sprocket.

3. The device of claim 1, wherein the leaf spring, cable and rotational element are arranged such that the leaf spring provides counter-rotational torque to the rotational element after the rotational element rotates past a predetermined angular position.

4. The device of claim 3, wherein the leaf spring provides the counter-rotational torque when the rotational element rotates such that the footplate rotates in a toe-down direction.

5. The device of claim 1, further including a pivot adjustably attached to the extended, hollow tubular structural member, the pivot being translatable along the extended, hollow tubular structural member such that it may contact the leaf spring at a plurality of positions along the leaf spring's length when the leaf spring is under tension.

6. The device of claim 5, further including an extension spring coupled to the pivot, the extension spring arranged to resist downward translation of the pivot, and to apply upward force to the pivot when extended.

7. The device of claim 6, wherein the pivot, extension spring, extended, hollow tubular structural member and leaf spring are configured such that the pivot tends to translate down when the device experiences deceleration of downward movement.

8. The device of claim 5, further including an actuator coupled to the pivot and operable to translate the pivot along the extended, hollow tubular structural member to vary a point of contact with the leaf spring along the leaf spring's length.

9. The device of claim 8, wherein the actuator is a motor.

10. The device of claim 8, wherein the actuator is a hydraulic piston coupled to a hydraulic bladder arranged in a toe region of the footplate.

11. A wearable assistive device, comprising:
- an extended, hollow, tubular structural member having a closed circumferential cross section, a first end and a second end defining a long axis through a center of the extended, hollow, tubular structural member;
- an attachment device coupled to the extended, hollow, tubular structural member and extending medially from the extended, hollow, tubular structural member, the attachment device configured to secure the extended, hollow, tubular structural member to a limb of a user;
- a rotational bearing disposed within the extended, hollow, tubular structural member and positioned on the long axis near the second end of the extended, hollow, tubular structural member;
- a rotational element coupled to the rotational bearing;
- a footplate dimensioned to support a foot of a wearer of the assistive device and coupled to the rotational element such that it may rotate with respect to the long axis of the extended, hollow, tubular structural member;
- a leaf spring attached to the extended, hollow, tubular structural member;
- a cable having a first end and a second end, the first end coupled to the leaf spring and the second end coupled to the rotational element, and
- a pivot adjustably attached to the extended, hollow tubular structural member, the pivot being translatable along the extended, hollow tubular structural member such that it may contact the leaf spring at a plurality of positions along the leaf spring's length when the leaf spring is under tension.

12. The device of claim 11, further including an extension spring coupled to the pivot, the extension spring arranged to resist downward translation of the pivot, and to apply upward force to the pivot when extended.

13. The device of claim 12, wherein the pivot, extension spring, extended, hollow tubular structural member and leaf spring are configured such that the pivot tends to translate down when the device experiences deceleration of downward movement.

14. The device of claim 11, further including an actuator coupled to the pivot and operable to translate the pivot along the extended, hollow tubular structural member to vary a point of contact with the leaf spring along the leaf spring's length.

15. The device of claim 14, wherein the actuator is a motor.

16. The device of claim 14, wherein the actuator is a hydraulic piston coupled to a hydraulic bladder arranged in a toe region of the footplate.

* * * * *